(12) United States Patent
Kobayashi et al.

(10) Patent No.: US 7,700,346 B2
(45) Date of Patent: Apr. 20, 2010

(54) TISSUE CHARACTERISTIC DETERMINATION APPARATUS

(75) Inventors: Hironori Kobayashi, Ono (JP); Hideki Ishihara, Miki (JP); Koichi Yamagata, Kobe (JP)

(73) Assignee: Sysmex Corporation, Kobe (JP)

( * ) Notice: Subject to any disclaimer, the term of this patent is extended or adjusted under 35 U.S.C. 154(b) by 633 days.

(21) Appl. No.: 11/520,984

(22) Filed: Sep. 14, 2006

(65) Prior Publication Data

US 2007/0077658 A1    Apr. 5, 2007

(30) Foreign Application Priority Data

Sep. 14, 2005    (JP)    ............................. 2005-266472

(51) Int. Cl.
*C12M 1/40* (2006.01)
*G01N 33/00* (2006.01)
*C12Q 1/00* (2006.01)
*G01N 33/574* (2006.01)

(52) U.S. Cl. ........................ 435/287.3; 422/68.1; 435/4; 435/7.23

(58) Field of Classification Search ........................ None
See application file for complete search history.

(56) References Cited

U.S. PATENT DOCUMENTS

| 6,413,731 | B1 * | 7/2002 | Borowsky et al. ............ 435/7.8 |
| 6,709,832 | B1 | 3/2004 | Von Knebel Doeberitz et al. |
| 2002/0164673 | A1 | 11/2002 | Ishihara et al. |
| 2007/0077658 | A1 * | 4/2007 | Kobayashi et al. ............ 436/63 |

FOREIGN PATENT DOCUMENTS

| JP | 2003-304884 | 10/2003 | | |
| WO | WO 99/42821 | 8/1999 | | |
| WO | WO2004076686 | * | 9/2004 | ............ 435/4 |

* cited by examiner

*Primary Examiner*—Jill Warden
*Assistant Examiner*—Timothy G Kingan
(74) *Attorney, Agent, or Firm*—Brinks Hofer Gilson & Lione

(57) ABSTRACT

The tissue characteristic determination apparatus capable of determining the characteristics of the tissues collected from a living organism is described, a representative one of which includes: a first data obtainer for obtaining first data reflecting the activity of first cyclin-dependent kinase contained in samples prepared from the tissues, a second data obtainer for obtaining second data reflecting the expression level of the first cyclin-dependent kinase, and a tissue characteristics information obtainer for obtaining information on the characteristics of the tissues based on first values obtained from the first and second data.

24 Claims, 28 Drawing Sheets

TISSUE CHARACTERISTIC DETERMINATION APPARATUS

FIELD OF THE INVENTION

The present invention relates to tissue characteristic determination apparatus and in particular, to tissue characteristic determination apparatus capable of determining correctly, for example, various kinds of characteristics of human tissues and of being suitably used with a method for determining cancer malignancy levels and/or a method for predicting the effectiveness of anticancer drug therapy.

BACKGROUND

Conventionally, cancer diagnosis methods, such as serological diagnosis that examines tumor markers in serum, as well as tissue diagnosis and cytological diagnosis using biopsy, have been publicly known. When, however, these methods are used in diagnosing cancers, the results from examinations may be obtained only at lower reliabilities or a variation inevitably occurs in diagnoses between diagnosticians and between medical institutions. Against this background, recently, molecular diagnosis based on proteins expressing in vivo has attracted much attention as one of methods for uniform cancer diagnosis with less variation in diagnosis between diagnosticians.

For example, a patent document PCT No. WO99/42821 proposes a diagnosis method that uses the expression levels of CDK1 and CDK4 of the sample, as well as P53 mutation level thereof, if necessary, as indexes. Another patent document U.S. Pat. No. 6,709,832B1 proposes a method for diagnosing cancer or precancerous condition based on an index of overexpression levels of CDK4, CDK6, and cyclin-dependent kinase inhibitor (CDK inhibitor). Further another patent document U.S. No. 2002/164673A1 proposes a method for measuring CDK activity values using fluorescence and a method for diagnosing cancers based on the values from the measurements thereof.

For example, a patent document PCT No. WO99/42821 discloses a method for predicting the effectiveness of an anticancer drug therapy, one of cancer therapy methods, involving; a step of identifying an anticancer drug biocompatibility marker gene based on the sensitivity of a cultured cancer cells line to the anticancer drug and a gene expression profile of the cells in its intact condition; and a step of predicting the biocompatibility of the anticancer drug with the identified anticancer drug biocompatibility marker gene and unknown specimens using the gene itself.

PCT No. WO99/42821, U.S. Pat. No. 6,709,832B1, and U.S. No. 2002/164673A1 disclose a method for determining whether test specimens have cancerated or proceeded into a precancerous condition, while they describe no method for determining malignancy grades of cancers, that is, for determining prognosis.

In addition, U.S. No. 2002/164673A1 discloses method for predicting the effectiveness of an anticancer drug therapy, though the results are obtained only at a lower accuracy when this method is used to predict the effectiveness of an anticancer drug therapy.

SUMMARY

The scope of the present invention is defined solely by the appended claims, and is not affected to any degree by the statements within this summary.

An object of the present invention, which has been achieved in view of this circumstance, is to provide tissue characteristic determination apparatus capable of obtaining information on the characteristics of the tissue useful in determining malignancy grades of cancers or predicting the effectiveness of an anticancer drug therapy at a higher accuracy.

The tissue characteristic determination apparatus according to the first aspect of the present invention determines the characteristics of a tissue taken from a living organism, wherein it has: a first data obtainer for obtaining first data reflecting an activity of a first cyclin-dependent kinase(CDK) contained in a sample prepared from the tissue; a second data obtainer for obtaining second data reflecting an expression level of the first CDK; and a tissue characteristic information obtainer for obtaining information on the characteristic of the tissue based on first value obtained from the first and second data.

The tissue characteristic determination apparatus according to the second aspect of the present invention determines the characteristics of a tissue, wherein it is capable of operating in a plurality of operation modes and has: a data obtainer for obtaining data reflecting CDK activity value or CDK expression level: a first tissue characteristic information obtainer for obtaining information on proliferation potency or malignancy level of cells contained in the tissue based on the data obtained by the data obtainer; a second tissue characteristics information obtainer for obtaining information on sensitivity of the tissue to irritant based on the data obtained by the data obtainer; and a mode selector for selecting operation mode from a first operation mode and a second operation mode, the first operation mode using the first tissue characteristic information obtainer and the second operation mode using the second tissue characteristic information obtainer.

The tissue characteristic determination apparatus according to the third aspect of the present invention determines the characteristics of a tissue, wherein it has: a first data obtainer for obtaining first data reflecting a first CDK activity value contained in a sample prepared from the tissue; a second data obtainer for obtaining second data reflecting a first CDK expression level contained in the sample; a first sample processor for applying a predetermined process to the tissue to obtain the first data by the first data obtainer; a second sample processor for applying a predetermined process to the tissue to obtain the second data by the second data obtainer; a tissue characteristics information obtainer for obtaining information on the characteristic of the tissue based on the first and second data; and a controller for controlling operations of the first and second sample processor so that the processing in both the first and second sample processor is executed in parallel.

DETAILED DESCRIPTION OF THE PREFERRED EMBODIMENT

Figure 1:
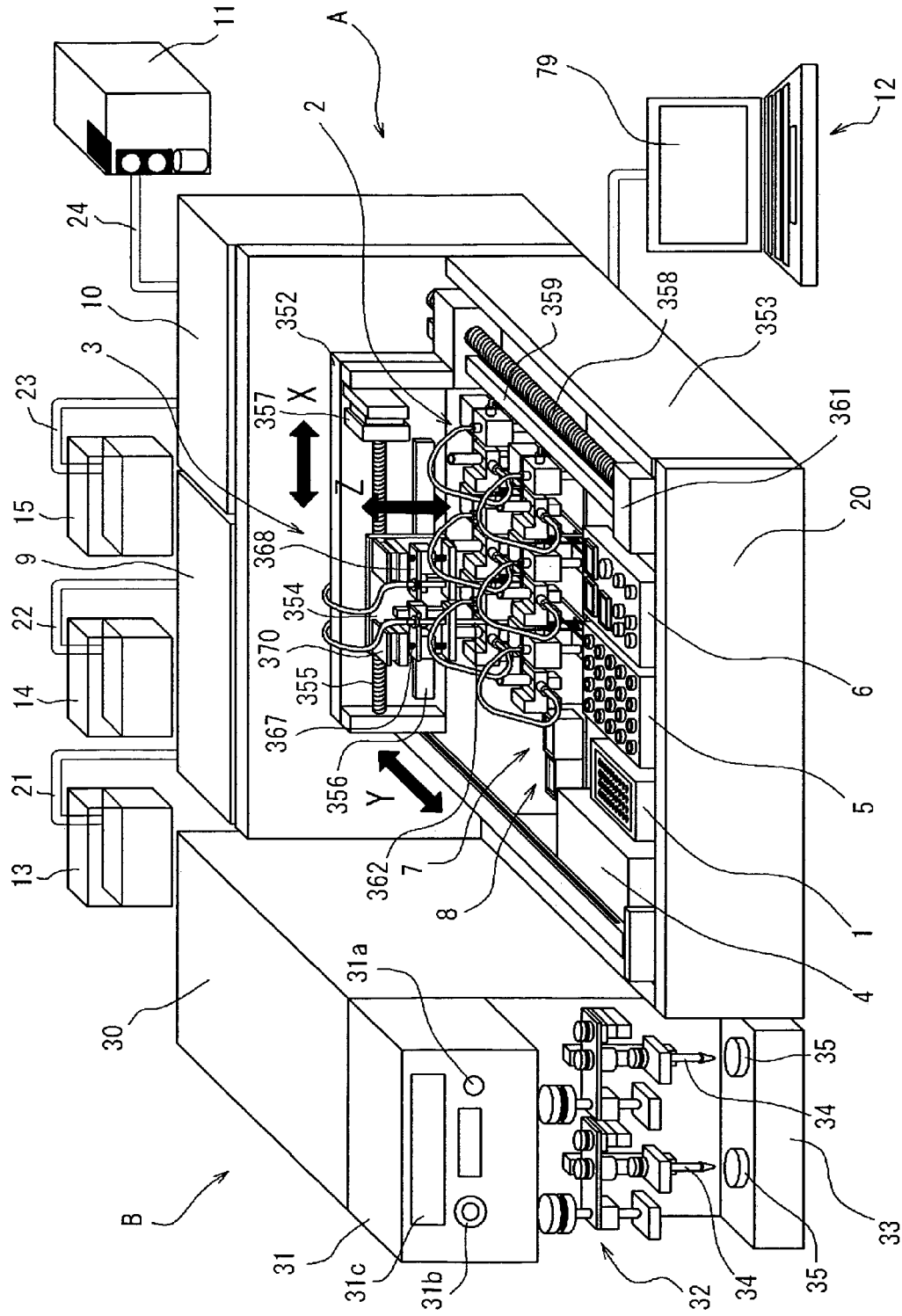
FIG. 1 is a perspective view explaining an embodiment of determination apparatus of the present invention.

Referring now to the drawings, embodiments of the tissue characteristic determination apparatus of the present invention (hereinafter, simply referred to as the determination apparatus) are in detail described.

According to the present embodiment, the determination apparatus may be suitable for use in measuring the expression levels and activity values of CDK to determine the malignancy grades (degrees of recurrence risk) of cancers based on the measured values and the effectiveness of anticancer drugs. Prior to describing said determination apparatus, first of all, [1] a method for determining the characteristics of mammalian tissues (those containing cancer cells) and [2] a method for predicting the effectiveness of anticancer drug therapy (a method for determining the sensitivity of tissues to ittitants) are described.

[1] Method for Determining the Characteristics of Mammalian Tissues

The method for determining the characteristics of mammalian tissues involves a step of measuring the expression levels and activity values of two or more kinds of cyclin-dependent kinase in mammalian tissues and a step of determining the characteristics of said mammalian tissues based on a CDK profile including a ratio of the activity value to expression level for a first cyclin-dependent kinase and a ratio of the activity value to expression level for a second cyclin-dependent kinase. The application of the determination method of the present invention to tissues containing tumor cells may make it possible to determine the characteristics of the tissues containing tumor cells and diagnose the malignancy grades of cancers. It should be noted that the CDK profile means information a certain tissue has including the ratio (for example, specific activity) of the activity value to expression level of at least one kind of CDK and/or values calculated from a plurality of activity values and expression levels of CDK (for example, a ratio of the ratio (A1) of the activity value to expression level for the first CDK to the ratio (A2) of the activity value to expression level for a second CDK (for example, A1/A2 or A2/A1)).

The mammals, characteristics of which tissues are determined by the determination method, are, but not in particular limited to, humans, especially those, whose clinical conditions need to be determined, more specifically, those, whose pathologic conditions of cancers need to be determined.

The tissues, of which characteristics are determined by the determination method, may be the living tissues from mammals, more specifically, supportive tissues including fibrous connective tissue, cartilage tissue, bone tissue, blood, and lymph node; epithelial tissue; muscular tissue; nervous tissue; or the like. The determination method is suitable for use in determining the characteristics of the tissues, on which pathological information need to be obtained as in tissues containing tumor cells contributing to damage to harmonization in the individuals, consequently inducing a dysfunctional control mechanism of cell-proliferation. The examples suitable for these tissues include those cancer tissues developed in organs including breast, lung, liver, stomach, large intestine, pancreas, skin, uterus, testis, ovaries, thyroid gland, parathyroid gland, lymphoid system, and bone marrow.

The characteristics of the mammalian tissues to be determined include the proliferating ability and malignancy levels of the cells contained in the target tissues. The proliferation ability of the cells means a growth activity level of the cells providing information on whether dysfunction has occurred in the proliferation control mechanism (whether the cells have been cancerated), as well as information on aneuploid cells. The malignancy level of the tumor cell means specifically metastatic and recurrent trends, and bad prognosis.

Herein, the term "recurrence" means a case where after part of an organ containing the malignant tumor cells is cut off, the same malignant tumor cells have developed in the rest organ; and a case where tumor cells separated from a primary lesion were carried to remote tissues (or a remote organ) and have autonomously proliferated therein (metastatic recurrence). In general, the recurrence level of a tumor is higher in the case where the tumor has recurred within five years since its curing. Focusing on the individual stages of tumor, the recurrence rate in Stage III is 50%, higher than that in Stage II (recurrence rate: 20%). Prognosis is to predict the progress and outcome of a disease. The prognosis level is worse with a higher mortality five or ten years after. Giving an example, the mortality rate is 50% in Stage III, indicating the prognosis worse than the in Stage II (mortality rate: 20%).

Cyclin-dependent kinase is a generic term representing a group of enzymes activated when binding to cyclin, to act their corresponding points of a cell cycle depending on the category of the enzymes. The CDK inhibitor is a generic term for group of factors, each of which binds to a cyclin-CDK complex to inhibit its activity.

Figure 16:
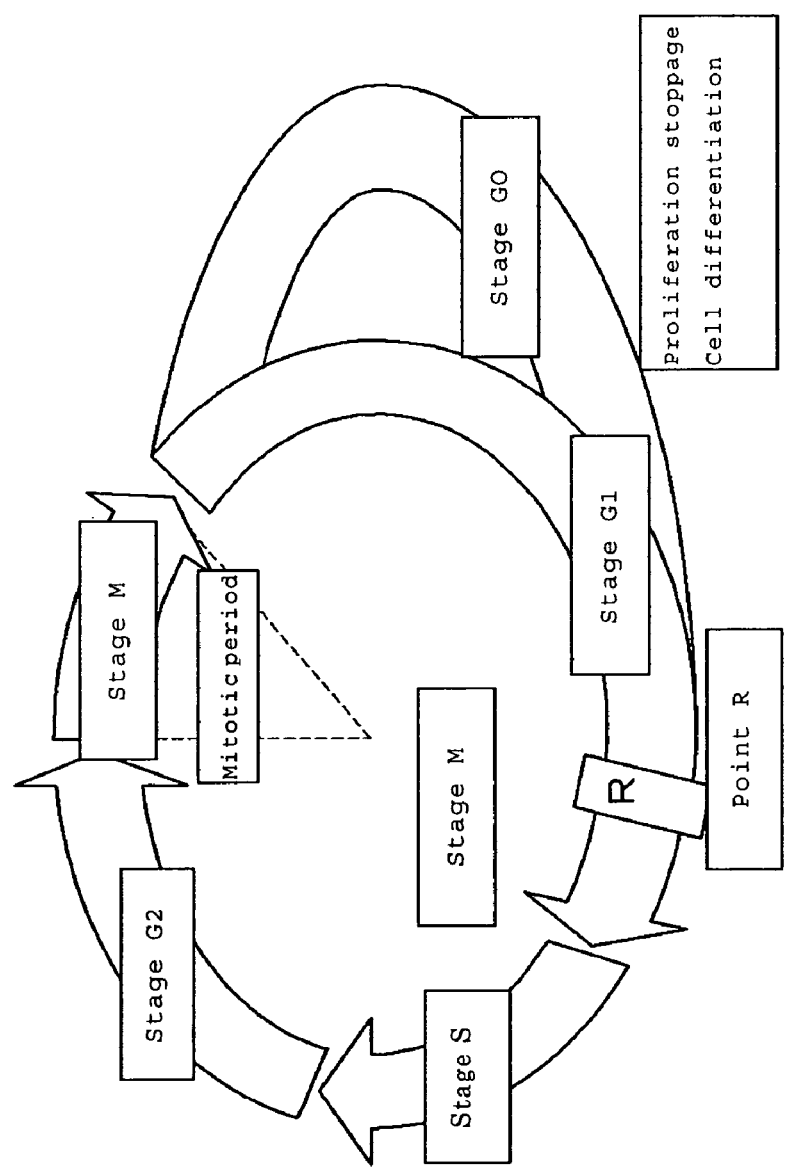
FIG. 16 is a view explaining a cell cycle.

Herein, the cell cycle, which is a cycle starting at a point when a cell proliferates until a point when returns to the starting point as two daughter cells, through a course of events, such as DNA replication, chromatid disjunction, nuclear fission, and cytoplasmic fission, are divided into four stages G1, S, G2, and M as shown in FIG. 16. Stage S is a DNA replication period and Stage M is a cell division period. Stage G1 is a period from the completion of mitotic division until the initiation of DNA synthesis, where preparatory checkup is made for entering Stage M. Once a critical point in Stage G1 (Point R in mammal cells) has passed, the cell cycle continues to take a round with no stop. Stage G2 is a period from the termination of DNA synthesis until the initiation of mitotic fission. In the cell cycle, main checkpoints are a point directly before the cell enters Stage S from Stage G1 and an entry point to mitotic fission in Stage G2. The checkpoint in Stage G1, which triggers the initiation of Stage S, in particular, is important. This is because once the critical point in Stage G1 has passed, the cell passes through the cell cycle S→G2→M→G1 with no stop even if proliferation signals are no longer given. It should be noted that some of the cells, which have stopped its proliferation, are put in its resting stage (G0) having DNA contents in Stage G1, dropping out from the cell cycle. These cells, however, when their proliferation is induced, may proceed to Stage S after a period slightly longer than Stage G1 in the cell cycle.

Cyclin-dependent-kinase (CDK) to be used with the determination method is preferably selected from a group of CDK1, CDK2, CDK4, CDK6, cyclin A-dependent-kinase, cyclin B-dependent-kinase, and cyclin D-dependent kinase. The cyclin A-dependent kinase is CDK, which is activated when binding to cyclin A. According to all we know now, it means both of CDK1 and CDK2. The cyclin B-dependent kinase is CDK, which is activated when binding to cyclin B. According to all we know now, it means CDK1. The cyclin D-dependent kinase is CDK, which is activated when binding to cyclin D. According to all we know now, it means both of CDK4 and CDK6.

According to all we know now, these CDKs bind to their corresponding cyclins to form cyclin-CDK complexes (hereinafter, simply referred to as activated CDKs) as shown in Table 1 to activate given periods in the cell cycle as shown in Table 1. For example, The CDK1 binds to cyclin A or B, the CDK2 to cyclin A or E, the CDK 4 and CDK6 to cyclin D1, D2, or D3 to be activated. On the other hand, the CDK activity may be inhibited by any of CDK inhibitors as shown in Table 1. For example, p21 inhibits CDK 1 or CDK2, p27 inhibits CDK2, CDK4, CDK6, and p16 inhibits CDK 4 and CDK6, respectively.

TABLE 1

| CDK | Combined cyclin | Combined CDK inhibitor | Action stage of activated CDK |
|---|---|---|---|
| CDK4 CDK6 | Cyclin D1 Cyclin D2 Cyclin D3 | p27, p16 | G1 |
| CDK2 | Cyclin E | p27 | Proceeds to S from G1 |
| CDK2 | Cyclin A | p21, p27 | Stage S activated |
| CDK1 | Cyclin A Cyclin B | p21, | Proceeds to M from G2 |
| Cyclin A-dependent-kinase | Cyclin A | p21, p27 | CDK1: proceeds to M from G2 CDK2: middle S stage |
| Cyclin B-dependent-kinase | Cyclin B | p21 | CDK1: proceeds to M from G2 |
| Cyclin D-dependent-kinase | Cyclin D | p27, p16 | CDK4, 6: G1 |

Out of the CDKs, the expression levels and activity values of two or more kinds of CDKs are measured and ratios (namely, CDK specific activity values or their reciprocal numbers) of the measured levels to the measured activity values to find CDK profiles. The CDK specific activity may be obtained by calculating CDK activity/CDK expression level. For this reason, specifically, the CDK profiles include profiles (CDK specific activity profiles) containing CDK specific activity values and profiles (reciprocal number of CDK specific-activity profiles) containing the reciprocal numbers of the CDK specific activity values.

The CDK activity value means the level of kinase activity (represented in units of U (unit)), which indicates kinase may phosphorylate how much substrate (for example, activated CDK1 and activated CDK2 phosphorylate Histon H1 and activated CDK4 and activated CDK6 phosphorylate Rb (Retinoblastoma protein)) when binding to its specific cyclin. This level may be measured by any the conventionally known enzyme activity measurement methods. Specifically, one of these methods involves a step of preparing samples containing an activated CDK from cell-dissolved solution, which is the sample to be measured; a step of trapping 32P into a substrate protein using ATP labeled with $^{32}P$ ($\gamma$-[$^{32}P$]-ATP); a step of measuring the quantity of labeled phosphorylated substrate; and a step of determining the quantity in reference to an analytical curve drawn using a standard product. Another method using no radioactive labels is disclosed in JB No. 335997/2002. This method involves a step of preparing samples containing a target activated CDK from cell-solubilized solution, which is sample to be measured; a step of reacting the substrate with adenosine 5'-O-(3-thiotriphosphate) (ATP-$\gamma$S); a step of introducing a monothiophosphate group into a serine or threonine residue of said substrate protein; a step of binding a labeling fluorescent substance or labeling enzyme to sulfur atom of introduced monothiophosphate group to label the substrate protein; a step of measuring the quantity of thiophosphate labeled (in the case where the labeling fluorescent substance, the quantity of fluorescent thiophosphate); and a step determining the quantity in reference to the analytical curve drawn using the standard product.

The samples to be used in measuring the CDK activity are prepared by specifically collecting the target CDK from the solution, in which the tissue to be measured is solubilized. In this case, an anti-CDK antibody specific to the target CDK may be used in preparing the samples. Alternatively, to measure the activity of specific cyclin-dependent kinase (for example, cyclin A-dependent kinase, cyclin B-dependent kinase, or cyclin E-dependent kinase), an anti-cyclin antibody may be used in preparing the samples. In any cases, the prepared samples will contain any other CDK than the activated CDKs. Giving an example, a complex combining a CDK inhibitor with the cyclin-CDK complex also may be contained. When the anti-CDK antibody is used, samples may contain any CDK alone, a CDK-cyclin and/or CDK inhibitor complex, and CDK-any other compound complex. Accordingly, the activity values are measured in units (U) of phosphorylated substrate in the presence of activated, inactivated CDKs, and mixed competitive reactions between them.

The CDK expression level, which is the target CDK quantity (a unit equivalent to the number of molecules) measured based on cell-solubilized solution, can be measured conventionally known methods for measuring the quantity of a target protein from a protein mixture. Giving an example, it may be measured by any of the methods such as the ELISA and WESTERN BLOT methods or may be measured by a method disclosed in JB No. 130871/2003. The target protein (CDK) may be trapped using its specific antibody. For example, the use of an anti-CDK1 antibody allows all the CDK1 contained in the cell (including a CDK alone, a CDK-cyclin and/or CDK inhibitor complex, and CDK-any other compound complex).

For this reason, the specific activity calculated by the expression is equivalent to the rate of activated CDKs out of CDKs contained in the cell, indicating the CDK activity level based on the proliferation state of an animal cell to be determined. The CDK specific activity calculated this way does not depend on a method for preparing sample to be measured. The sample to be measured (cell-solubilized solution) prepared by the method for preparing sample to be measured, in particular prepared from a biopsy material is subject to the quantity of noncellular tissue contained in an actually collected tissue, for example, extracellular matrix. For this reason, it is of great significance that the specific activity values or their reciprocal numbers are used to avoid such a problem. Such specific activity values or their reciprocal numbers have higher correlation with clinical characteristics compared to the conventional simple activity values.

Examination of the CDK profiles containing two or more kinds of CDK specific activities or their reciprocal numbers gives information on which CDK activity is dominant over the other ones. Based on this information, the percentage of cells may be determined at any stage in the cell cycle or the stage in the cell cycle, at which the percentage of cells is dominant, may be known.

Now, the method for determining the characteristics of mammalian tissues (especially, tissues containing cancer cells) is described focusing on the CDK specific activity profiles containing CDK specific activity values. The kind of CDK, of which specific activity is to be measured, may be selected according to the kind of characteristic need to be determined. In general, cancer cells, escaping from normal proliferation control, actively proliferate. Thus, the percentage of cells in Stages S and G2 is considered to be higher suggesting the cells having been cancerated. Cancers stemming from these types of cancer cells show rapid progress, namely being of malignant type. Aneuploid cells may grow when they have undergone abnormal Stage M or when they have proceeded directly to Stage G1 bypassing Stage M and then entering Stage S. Accordingly, a lower percentage of cells in Stage M implies malignant cancers. For this reason, CDK1 is used as first cyclin-dependent kinase and CDK2 as second cyclin-independent kinase to classify the cells into groups in the ascending order of CDK1 values. In the group of cells having similar CDK1 specific activity values, the CDK2 specific activity values reflect the percentage of cells in Stage S. If the number of cells in Stage S is large, it may be determined that the tissue composed of said cells is clinically malignant, namely a malignant cancer with worse prognosis, meaning that it is subject to metastasis.

Alternatively, to determine the malignancy level of the cells, the percentage of cells in the given stage in the cell cycle may be estimated based on the kinds of CDKs and their known actions in reference to the CDK specific activity profiles containing two or more kinds of CDK the specific activity values, or the CDK specific activity profiles containing the specific activity values for two or more kinds of CDKs, which have been predetermined using their corresponding normal tissue cells as standard cells, is found for comparison with those of the normal cells. For the CDK specific activity profiles, the ratio of the specific activity value of one kind of cyclin-dependent kinase to that of another kind of cyclin-dependent kinase is preferably used. In this case, the ratio between two kinds of cyclin-dependent kinase is compared with the given threshold corresponding to said ratio to determine the characteristics of the tissue.

Thresholds used with the determination method may be appropriately determined according to the types of cells to be measured and the characteristics to be determined. For the settings of the thresholds, the value for the ratio between the specific activity values, which gives an indication of borderline for determining the characteristics, may be selected based on the a lot of cells involved in determining the target characteristics, a database of individuals, and a database of CDK specific activity values of the cells. For example, tumor cells, for which malignancy levels were determined by pathologists, have been collected from a plurality of patients. The ratios between the specific activity values of two kinds of CDKs considered to have correlation each other are obtained and the obtained ratios are arranged in the descending order. A median obtained by bisecting the group of ratios may be used as the threshold.

[2] Method for Predicting the Effectiveness of Anticancer Drug Therapy (Method for Determining the Sensitivity of Tissues to Irritants)

The method for predicting the effectiveness of anticancer drug therapy involves; a step of comparing at least one parameter selected from a group of the activity values, expression levels, and ratios between the activity values and expression levels for the cyclin-dependent kinase in the tumor cells collected from patients with the threshold corresponding to a selected parameter; and a step of predicting the effectiveness of anticancer drug therapy on the patients based on the results of the comparison step.

The effectiveness of therapy to be predicted by the prediction method includes those of pre-operative and post-operative therapy. For pre-operative therapy, such a case is determined to be effective that after an anticancer drug has been continuously administered to the patients with a primary lesion, the primary lesion reduces or disappears. For post-operative therapy, such a case is determined to be effective that the same type of cancer does not recur after an anticancer drug has been continuously administered since extirpative surgery. For post-operative therapy, it gives an indication of recurrence whether the anticancer drug is effective for invisible metastatic cancer or the like.

The tissues to be used as samples in the prediction method are those containing tumor cells collected from patients. For post-operative therapy, such tissues available through extirpative surgery can be used. For pre-operative therapy, the tissues (biopsy tissues) collected from the tumor tissues of the patients or the like may be used.

The cyclin-dependent kinase (CDK) to be used with the prediction method includes CDK1, CDK2, CDK4, CDK6, cyclin A-dependent kinase, cyclin B-dependent kinase, and cyclin D-dependent kinase, out of which appropriate ones may be selected according to the types of cancers and anticancer drugs. This means that cancers may be classified into many categories and the effectiveness of the anticancer drug therapy largely depends on the characteristics related to the cell cycles of the cancer cells of the respective patients.

Target cancers include breast cancer, stomach cancer, colon cancer, esophageal cancer, prostate cancer, and the like. The anticancer drugs for breast cancer include a CMF group (three-drug combined administration of cyclophosphamide, methotrexate, and fluorouracil), taxane anticancer drugs such as docetaxel and paclitaxel, CE (two-drug combined administration of cyclophosphamide and epirubicin), AC (two-drug combined administration of doxorubicin and cyclophosphamide), CAF (three-drug combined administration of fluorouracil, doxorubicin, and cyclophosphamide), FEC (three-drug combined administration of fluorouracil, epirubicin, and cyclophosphamide), two-drug combined administration of trastuzumab and paclitaxel, capecitabine, and the like. The anticancer drugs for stomach cancer include FAM (three-drug combined administration of fluorouracil, doxorubicin, and mitomycin C), FAP (three-drug combined administration of fluorouracil, doxorubicin, and cisplatin), ECF (three-drug combined administration of epirubicin, cisplatin, and fluorouracil), two-drug administration of mitomycin C and tegafur, two-drug combined administration of fluorouracil and carmustine, and the like. The anticancer drugs for colon cancer include two-drug combined administration of fluorouracil and leucovorin, two-drug combined administration of mitomycin and fluorouracil, and the like. The anticancer drugs for ovary cancer include TP (two-drug combined administration of paclitaxel and cisplatin), TJ (two-drug combined administration of paclitaxel and carboplatin), CP (two-drug combined administration of cyclophosphamide and cisplatin), CJ (two-drug-combined administration of cyclophosphamide and carboplatin) and the like.

One or two selected from parameters of CDK activity values, CDK expression levels, and the ratio between the CDK activity values and expression levels give an indication for determination. The ratio of the activity values to the expression levels may be the CDK specific activity value obtained by calculating CDK activity value/CDK expression level or may be the value obtained by calculating CDK expression level/CDK activity value. The parameters can be compared with the given thresholds to determine whether anticancer drugs are effective. Herein, the parameters selected from the activity values, the expression levels, and the ratio between the activity values and the expression levels are those selected appropriately according to the kinds of the anticancer drugs and the type of cancer. To obtain the parameters to be used in determining the effectiveness of anticancer drugs, the CDK activity values and expression levels of the tumor cells collected from the cancer patients, for whom anticancer therapy was applied and the effectiveness of therapy was known, prior to cancer therapy and stored are measured, the results of anticancer drug therapy are analyzed for the respective parameters, and the parameters having correlation with the results of anticancer drug therapy are selected.

The parameters to be compared with the thresholds may be one parameter of the given CDK or may be a pair of two parameters of it. When the two parameters are selected, the individual parameters should be compared with their corresponding thresholds. Either one kind (effectiveness prediction method I) or two or more kinds (effectiveness prediction method II) of CDKs may give an indication for determination.

When two or more kinds of CDKs, the individual parameters of a plurality of CDKs may be compared with their corresponding thresholds to predict the effectiveness of anticancer drug therapy based on the combination of the results of comparison among kinases (effectiveness prediction method II-1). In this case, the parameters of the plurality of CDKs to be compared with their corresponding thresholds may be of the same kind (for example, expression level) or may be of different kinds (for example, for one CDK, its expression level is compared with its threshold while for another CDK, its activity value is compared with its corresponding threshold).

When a plurality kind of CDKs are used, the effectiveness of anticancer drug therapy may be predicted; by predicting the effectiveness on first CDK(s) using the effectiveness prediction method I; and comparing the parameters selected from the activity values, expression levels, and ratio between the activity values and expression levels for the CDK other than the first CDK(s) with their corresponding thresholds concerning the tumor cells, for which effectiveness of anticancer drug therapy was determined to be doubtful by the effectiveness prediction method I (effectiveness prediction method II-2). In the effectiveness prediction method II-2, the CDK other than the first CDK(s) may be one kind of CDK (a second CDK) or may be a plurality kind of CDKs (third, fourth ... CDK). When the plurality kinds of CDKs are used, at least one selected from the parameters of the activity value, expression level, and ratio between the activity value and expression level for each CDK should be compared with the threshold corresponding to said parameter and based on the combination of the results of comparison to predict the effectiveness of anticancer drug therapy on the patients.

For the second CDK, the parameters to be used in determining the effectiveness of anticancer drug therapy are selected from the group. Only one parameter may be selected or two parameters may be selected for comparison with their corresponding thresholds. To make measurement on the different CDKs, namely the plurality kinds of CDKs, the second, third, fourth CDKs, the same kind, such as the expression level, of parameters may be used or different kinds of parameters (for example, the expression level is used for the second CDK while the activity value for the third CDK) may be used to determine the effectiveness of anticancer drug therapy.

The effectiveness prediction method II is has an advantage in that it has a higher percentage of right answers. The use of the effectiveness prediction method II is of significance because in many cases, anticancer drug therapy is determined to be effective by the effectiveness prediction method II-II even if it is not determined to be effective by the effectiveness prediction method I. The efficacy of anticancer drugs includes two levels; at one level, the progress of cancer is prevented and at another level, the tumor is reduced in size to improve the disease state. The effectiveness prediction method II, especially the effectiveness prediction method II-II enables the effectiveness to be predicted considering the efficacy level of anticancer drug therapy.

According to the effectiveness prediction methods, the effectiveness of anticancer drug therapy on the patients may be predicted based on the combination of the results obtained by comparing the expression levels of CDK(s) with their corresponding to their thresholds and the results obtained by comparing the expression levels of the cyclin-dependent kinase inhibitor (CDK inhibitor) with their corresponding thresholds (effectiveness prediction method III). The CDK inhibitor composed of a group of factors, which bind to cyclin-CDK complexes to inhibit their activity, are classified into an INK 4 family and a CIP/KIP family. With the effectiveness prediction methods, the CIP/KIP family, especially p21, is preferably used. p21 is an inhibitor, which inhibits the progress of cancer at both the checkpoints in Stages G1 and G2 in the cell proliferation cycle, affording enough time to repair damaged DNA.

According to the effectiveness prediction method III, the effectiveness of anticancer drug therapy may be predicted based on the combination of the results obtained by comparing the given CDK parameters with their corresponding thresholds and the results obtained by comparing the CDK-inhibitor expression level with their corresponding thresholds or anticancer drug therapy considered to be highly effective may be selected by comparing the given CDK parameters with their corresponding thresholds to determine the effectiveness of anticancer drug therapy in a first step (effective prediction method I) and then by comparing the expression level of the CDK inhibitor with its corresponding threshold concerning the tumor cells, for which anticancer drug therapy has not been determined to be effective, in a second step.

Her2 and p21 have been reported as effectiveness prediction factors for CMF administration therapy. The clinical trial by The International Breast Cancer Study Group (IBCSG) suggested that CMF administration was not effective for breast cancer patients with Her2 over-expressed, and demonstrated that the disease-free survival for a group of the patients with higher expression of p21 is significantly lower than that for a group of the patients with lower expression of p21. Both the Her2 and p21, however, are the factors for predicting the group of the patients, for whom the effectiveness of CMF therapy is low, and no factor for actively predicting the group of the patients, for whom the effectiveness is high, has been reported. In contrast, according to the prediction methods, not only the effectiveness of anticancer drug therapy is actively demonstrated but also such a case may be indicated by making the thresholds stricter that almost 100% of effectiveness may be expected.

In the prediction methods, the thresholds are the values specified appropriately based on the kinds of anticancer drugs and the types of cancers. More specifically, the values are set so that the cases, in which the anticancer drug therapy is determined to be effective based on the parameters having correlation with the large amount of results of anticancer drug therapy, may be selected by examining the relationship between a large amount of results of anticancer drug therapy, in which given anticancer drugs were administered to the patients with given types of cancers, and the parameters. Preferably, the thresholds are set so that only the cases, for which all the results of anticancer drug therapy are effective, may be selected. Thus, the thresholds are set based on the actual results of clinical anticancer drug therapy, allowing the effectiveness to be determined at a higher accuracy. By increasing the number of results of clinical anticancer drug therapy used for setting the thresholds, the accuracy of effectiveness determination may be improved. The results of anticancer drug therapy include those obtained by examining any variation in tumor size caused by continuous application of given anticancer drug therapy or by continuously examining any recurrence over five to six years.

It should be noted that the ratio represented by the CDK activity value/CDK expression level (CDK specific activity value) or the CDK expression level/CDK activity value is equivalent to the percentage of activated CDKs out of all the CDKs contained in the cell, indicating the CDK activity level based on their own proliferation state shown by the tumor cells to be measured and does not depend on the method for preparing the samples to be measured. The cell solubilized solution prepared by method for preparing sample to be measured, especially from the biopsy material is subject to the quantity of noncellular tissues contained in the actual tissues collected, for example, extracellular substrate. Accordingly, using the ratio between the CDK expression level and activity values, inevitable influences may be eliminated during preparation of sample to be measured, enabling the effectiveness to be determined at a higher accuracy even if the determination method focusing on proteins is used.

The expression level of the CDK inhibitor means the quantity (the unit corresponding to the number of molecules) of the target CDK inhibitor to be measured from the cell-solubilized solution, which may be measured by any of conventionally known methods for measuring the quantity of a target protein from a protein mixture. For example, the ELIZA method or the WESTERN BLOT method may be used. The target protein (CDK inhibitor) may be trapped using its specific antibody. Either a monoclonal or polyclonal antibody may be used provided that it can bind specifically to the target protein. For example, to trap p21, either an anti-p21 monoclonal antibody or an anti-p21 polyclonal antibody may be used.

Next, the above-mentioned determination apparatus according to one embodiment of the present invention, which is capable of suitably applying the [1] method for determining the characteristics of mammalian tissues and [2] method for predicting the effectiveness of anticancer drug therapy, is described.

FIG. 1 is a perspective view explaining determination apparatus A according to one embodiment of the present invention. The determination apparatus A, which is capable of measuring the activity values and expression levels of cyclin-dependent kinases (CDKs) contained in the tissues to determine the malignancy levels (the level of recurrence risk) of the human cancer cells and the effectiveness of (sensitivity to) anticancer drugs based on the measured values, is composed mainly of; a detecting member 4, a chip setting member 1, a first reagent setting member 5 and second reagent setting member 6, which are disposed in a front part of an apparatus body 20; an activity measurement unit 2, a waste bath 7 for collecting waste solution, and a pipette washing bath 8 for washing a pipette, which are disposed in the rear part of the apparatus body 20; a dispensing mechanism 3 disposed in a upper part of the apparatus body 20, which is capable moving the pipette in three directions (X, Y, and Z directions); a fluid member 9 and an electronic board 10 disposed on the back of the apparatus body 20; and a personal computer 12, which is a control means connected to the detecting member 4 and the electronic board 10 for communication between each other. In addition, the determination apparatus A according to this embodiment has a pure water storage tank 13, a cleaning liquid tank 14, a waste tank 15, and a pneumatic source 11. The pure water storage tank 13 containing pure water for cleaning flow channel at the completion of measurement is connected to a fluid member 9 by means of piping 21. The cleaning liquid tank 14 containing the cleaning liquid for cleaning the pipette is connected to the pipette washing bath 8 by means of piping 22. The waste tank 15 for collecting waste solution is connected to the waste bath 7 by means of piping 23. Moreover, a solubilization apparatus B for obtaining specimens capable of being processed in the determination apparatus A from living samples is arranged in parallel with the determination apparatus A.

Now, generally following the procedures of the determination method or effectiveness prediction method described above, the solubilization apparatus B and the determination apparatus A are described.

[Solubilization Apparatus]

The solubilization apparatus B, which prepares the liquid specimens capable of being processed in the determination apparatus A from living samples such as the tissues collected from the patients prior to the processing in that determination apparatus A, is composed mainly of a housing 30, an operating member 31 disposed in the upper front of the housing 30, a driving member 32 equipped with a pair of pestel 34 for pressing or grinding the living samples, and a specimen setting member 33 with an inserted eppen tube 35 for containing the living samples.

The driving member 32 is capable of moving the pestle 34 up and down while rotating it, and thereby, the living samples are pressed or ground injected in the eppen tube 35. The housing 30 contains a controlling member (not shown in the figure) for controlling the movement of the driving member 32 therein.

The operating member 31 has an operating button 31*a*, an operation LED 31*b*, a display member 31*c* for indicating the apparatus state, error message, and the like therein. The specimen setting member 33 contains a cooling means (not shown in the figure), which keeps the living samples in the eppen tube inserted into a pocket on the upper surface of the specimen setting member 33 at a constant temperature.

The supernatant liquid of living samples after being solubilized in the solubilization apparatus B and then separated in a centrifuge (not shown in the figure) is collected into given specimen vessels and then set in the first reagent setting member 5 of the determination apparatus A.

[First Reagent Setting Member]

In the first reagent setting member 5, besides the specimen setting member 33, the cooling means (not shown in the figure) is disposed for keeping the specimens in the vessels, such as screw caps, inserted in the pocket on the upper surface of the first reagent setting member 5, various types of antigens including CDK 1 antigens (calibration 1), CDK 2 antigens (calibration 2), a variety of fluorescence-labeled antibodies including fluorescence-labeled CDK 1 antibodies and fluorescence-labeled CDK 2 antibodies, and the like, at a constant temperature. According to this embodiment, 20 pockets in total are arranged in five columns and four rows, allowing up to 20 vessels, such as screw caps, to be set therein.

[Second Reagent Setting Member]

Next to the first reagent setting member 5, the second reagent setting member 6 is disposed. Like the first reagent setting member 5, in the second reagent setting member 6, a plurality of pockets are arranged for setting the vessels, such as eppen tube and screw caps, containing a buffer, substrate solution, fluorescence enhancing reagent, or the like.

Prior to the processing in the determination apparatus A, chips for protein immobilization are set in the chip setting member 1 and columns are set in the activity measurement unit 2.

[Chip Setting Member]

Figure 2:
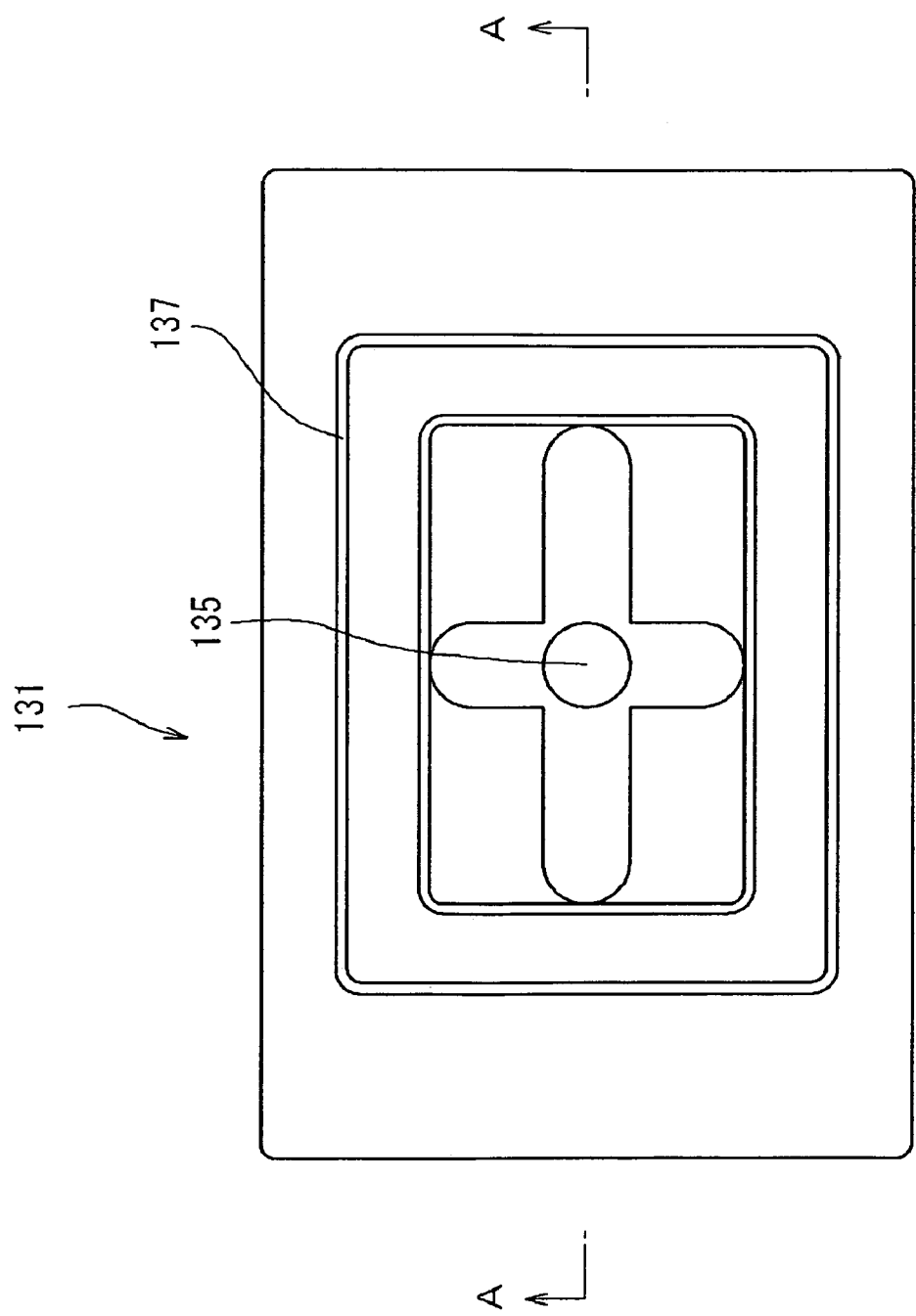
FIG. 2 is a top view showing a chip setting member in the determination apparatus shown in FIG. 1.
Figure 3:
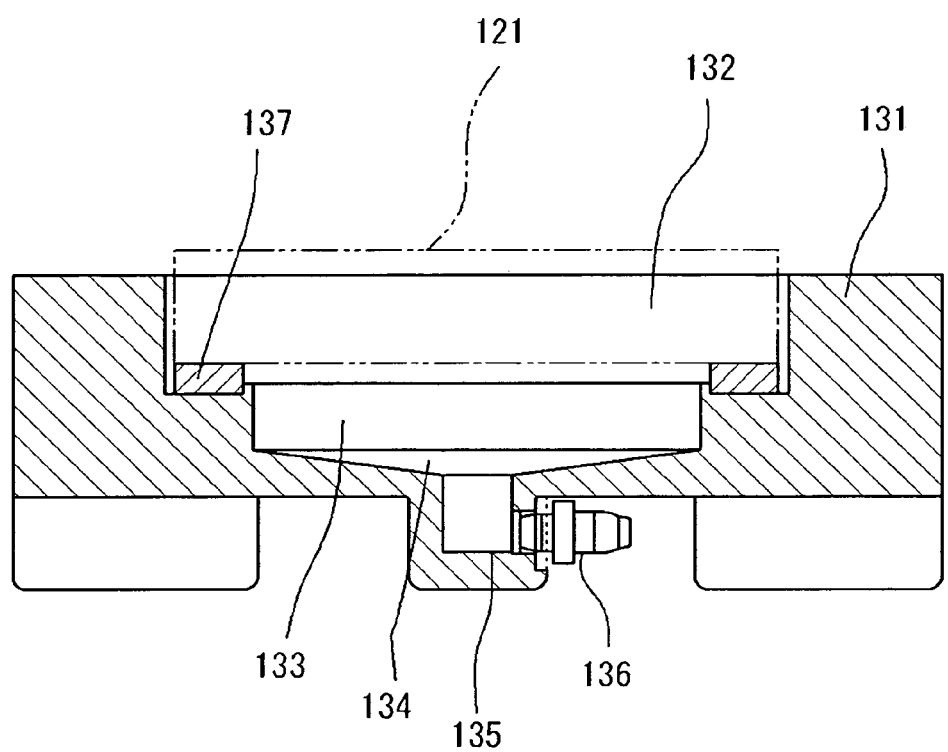
FIG. 3 is a sectional view taken in the direction of the arrows substantially along the line A-A of FIG. 2.

The chip setting member 1 composed of aluminum blocks has a pocket 132 for mounting the chip 121 for protein immobilization on its upper surface and a suction inlet 135 at its bottom, as shown in FIGS. 2 to 3. More specifically, the chip setting member 1 has the rectangular first pocket 132 on the upper surface and a similarly rectangular second pocket 133 at the bottom of the first pocket 132. At the bottom of the first pocket 132, a rectangular frame of rubber flexible gasket 137 is disposed on the circumference of the second pocket 133.

The second pocket 133 has a cross-shaped groove 134 at the bottom thereof and the suction inlet 135 at the center of the bottom thereof, the bottom of the groove 134 inclines toward the center from the circumference of the second pocket 133, proceeding to the deeper point. The suction inlet 135 links to a nipple 136 disposed for connecting to an external suction pump (not shown in the figure). The chip 121 for protein immobilization, which will be described in detail later, is horizontally loaded via a bottom gasket 137 of the first pocket 132. Once sample solution containing protein has been injected or dispensed into each of the wells of the chip 121 for protein immobilization, the suction pump (not shown in the figure) connected to the nipple 136 initiates its operation.

Accordingly, as soon as the chip 121 for protein immobilization is hermetically adsorbed to the bottom of the first pocket 132 via the gasket 137, sample solution in each well is sucked via a porous membrane, which will be described in detail later, to form the immobilized protein to be measured on the porous membrane. In this case, a fixing member for fixing the chip 121 for protein immobilization to the bottom of the first pocket 132 by pressing against the pocket may be disposed in the chip setting member 1.

As shown in FIGS. 4 to 8, the chip 121 for protein immobilization is composed of a porous membrane 122, an upper template 101 and a lower template 102 for supporting the porous membrane 122 between them. The chip 121 for protein immobilization acts as a second contact means for bringing antibody solution containing an antibody for cyclin-dependent kinase into contact with the living samples (specimens).

Figure 4:
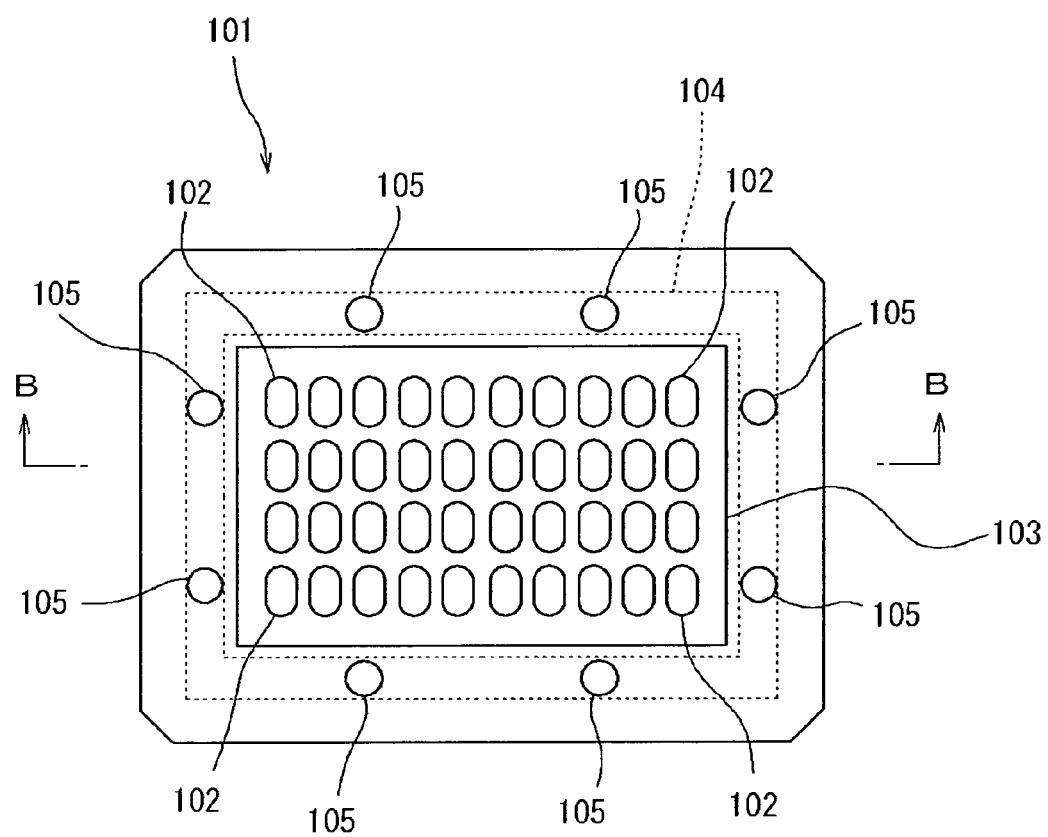
FIG. 4 is a top view of an upper template of a protein immobilization chip mounted in a chip setting member of the determination apparatus shown in FIG. 1.
Figure 5:
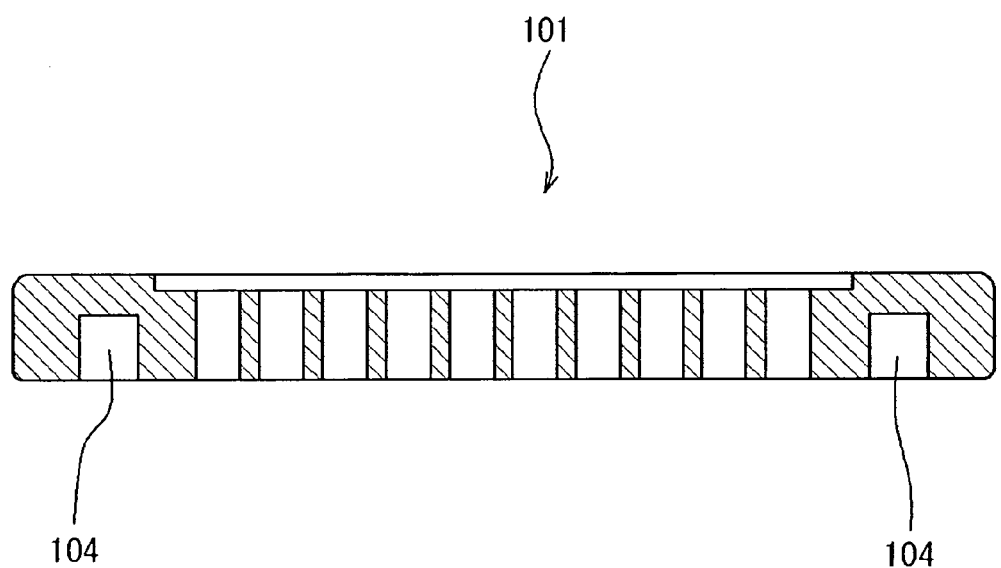
FIG. 5 is a perspective sectional view taken in the direction of the arrows substantially along the line B-B of FIG. 4.
Figure 6:
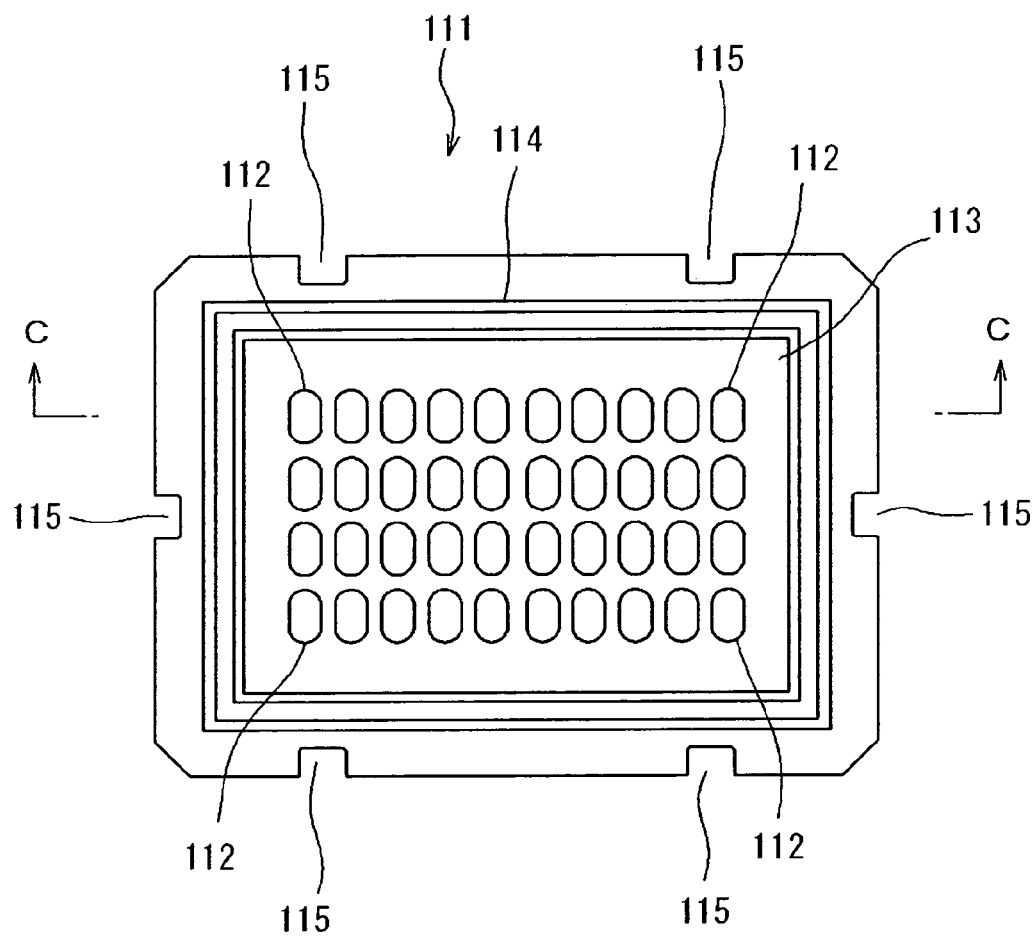
FIG. 6 is a top view of a lower template of the protein immobilization chip mounted in the chip set of the determination apparatus shown in FIG. 1.
Figure 7:
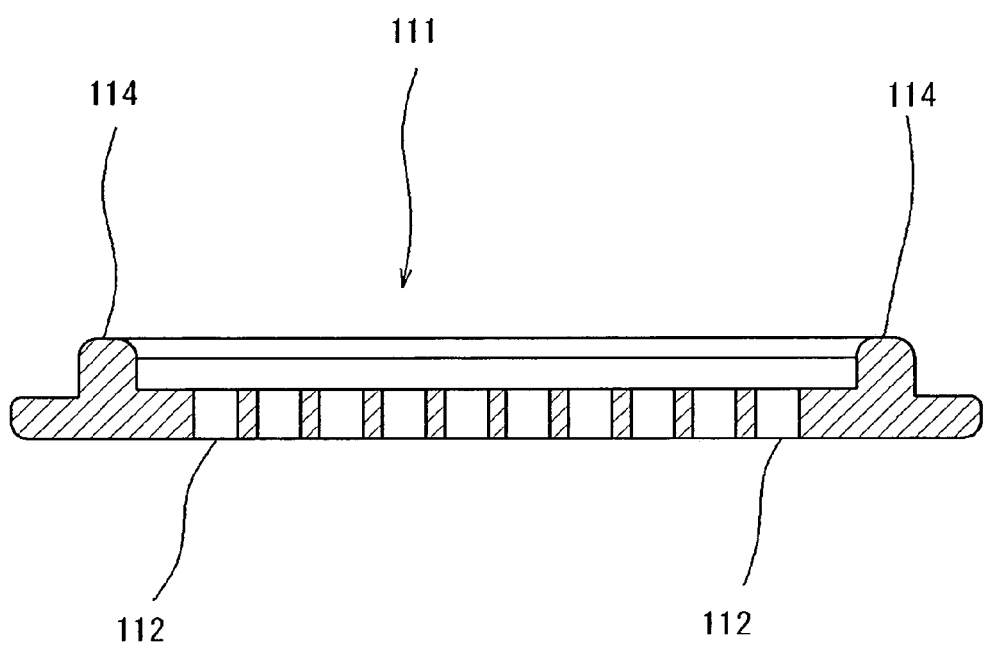
FIG. 7 is a perspective sectional view taken in the direction of the arrows substantially along the line C-C of FIG. 6.

As shown in FIGS. 4 to 5, on the rectangular plate of upper template 101, a matrix of 40 rectangular through-holes 102 arranged in four columns and ten rows are formed. At the bottom of the upper template 101, a groove (pocket) 104 running along the circumference of the matrix of 40 through-holes 102 is formed. This groove 104 defines a rectangular porous membrane setting area 103 therein. At the bottom of the groove 104, eight jig through-holes 105 are formed.

On the other hand, on the rectangular plate of lower template 111, a matrix of 40 rectangular through-holes 112 are arranged in four columns and ten rows at the positions corresponding to those of the through-holes 102 of the upper template 101. The through-holes 112 have the same shape area as those of the through-holes 102.

On the upper surface of the lower template 111, a ribbed convex 114 running along the circumference of the matrix or 40 through-holes is formed at the position corresponding to that of the groove 104. The convex 114 defines the rectangular porous membrane setting area 113 therein. On the circumference of the lower template 111, six notches are formed 115. The upper template 101 and lower template 111 may be made of, for example, a vinyl chloride resin.

Figure 8:
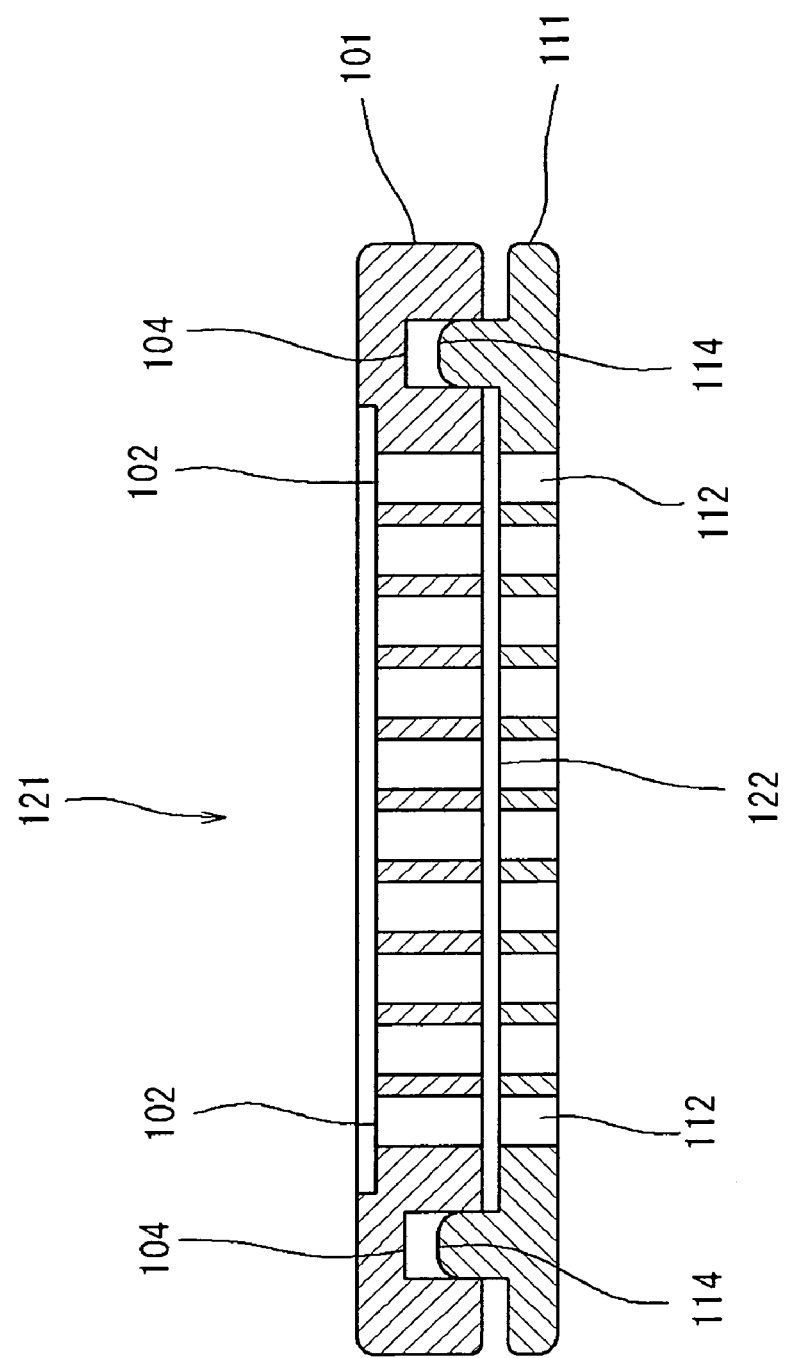
FIG. 8 is an assembly sectional view of the upper template shown in FIG. 4 and the lower template shown in FIG. 6.

FIG. 8 shows the cross section of the chip 121 for protein immobilization. As shown in the figure, the upper template 101 and lower template 111 are overlapped and the convex 114 is detachably pressed in the groove 104. Thereby, the through-holes 102 have the same axis as that of the through-holes 112.

The rectangular hydrophobic membrane 122 is inserted between the porous membrane setting areas 103 and 113 and uniformly compressed when the convex 114 is pressed in the groove 104. Accordingly, the porous membrane 122 is hermetically defined by the through-holes 102, forming the same number of wells (solution vessels) as that of the through-holes 102.

[Activity Measurement Unit]

As shown in FIGS. 9 to 12, the activity measurement unit 2 is composed of a plurality of sample preparing members 211, each being equipped with the column 201 and a fluid manifold 213 and used in measuring the CDK activity values.

Figure 9:
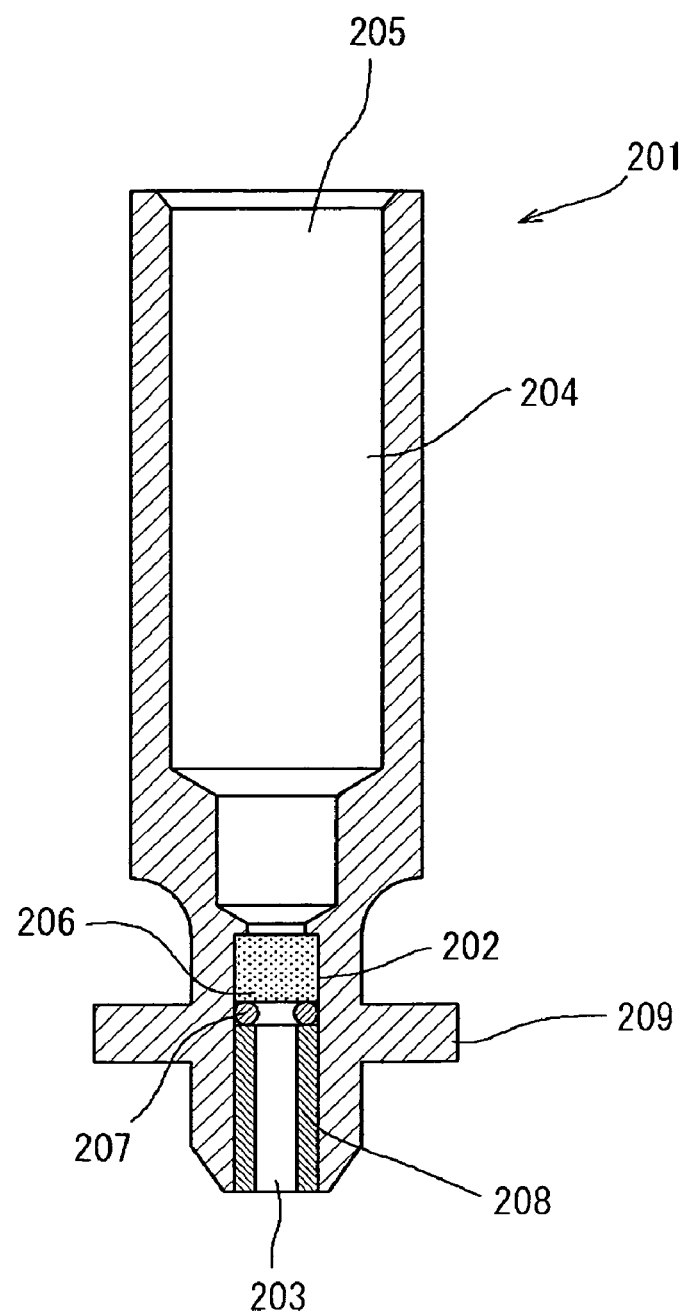
FIG. 9 is a sectional view explaining a column of a sample preparation member of an activity measurement unit in the determination apparatus shown in FIG. 1.

As shown in FIG. 9, the column 201 is composed of a cylinder made of the vinyl chloride resin and has a carrier holding vessel 202 for holding a carrier support 206 to be used in isolating the target protein in the liquid samples, an liquid introducing member 203 for introducing a liquid sample into the carrier holding vessel 202, and a liquid reservoir 204 for receiving the liquid sample from the carrier holding vessel 202 and reserving the received liquid. The column 201 acts as a first contact means for bringing the substrate solution containing a given substrate into contact with the living samples (specimens).

The liquid reservoir 204 of the column 201 has an opening 205 capable of externally injecting or collecting the liquid samples on its upper part. The carrier support 206 composed of a cylindrical monolith silica gel, which has a structure combining a 3D network of skeleton and gaps, unlike a particle support. A given CDK antibody is fixed to the monolith silica gel. The carrier support 206 is inserted into the carrier holding member 102 from the lower opening of the column 201 and then flexibly pressed in by means of a fixing pipe 208 via an O ring 207 for support. It should be noted that the fixing pipe 208 is pressed in from the lower opening of the column 201 and the fixing pipe 208 and the hole of the O ring 207 form the liquid introducing member 203.

At the lower end of the column 201, a loading flange 209 is formed for loading the column 201 into the sample preparing members 211 and fixing them. The flange 209 is a rectangular one with notches formed in parallel at the ends of a disk-shaped flange with D in diameter so that the widths W of the ends may be W<D.

Figure 10:
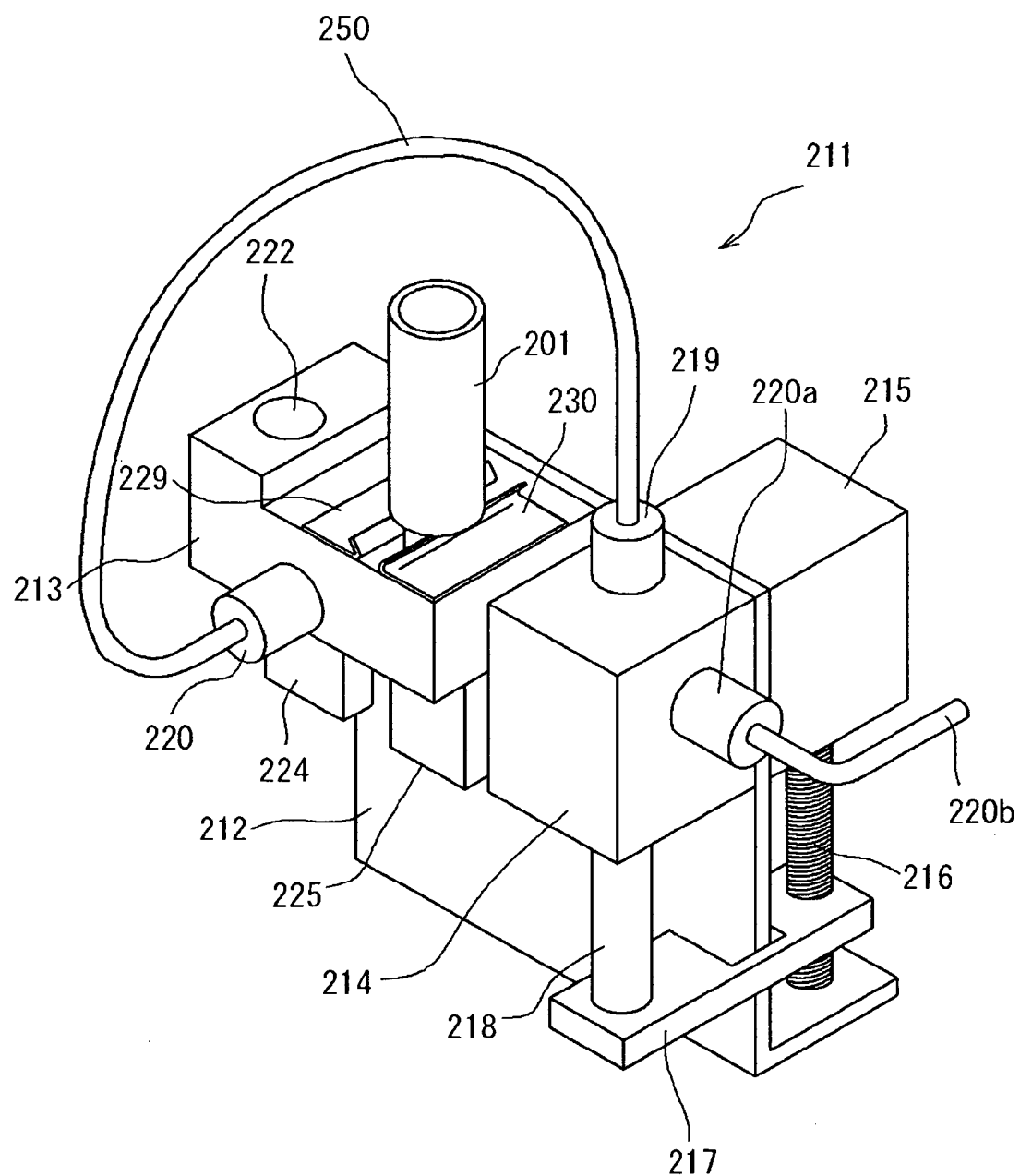
FIG. 10 is a perspective view of the sample preparation member of the activity measurement unit of the determination apparatus shown in FIG. 1.

FIG. 10 is a perspective view of the sample preparing members 211. As shown in the figure, the sample preparing members 211 has an L-shaped supporting plate 212, to which the fluid manifold 213, the syringe pump 214, and a stepping motor 215 with a decelerator are fixed.

A screw shaft 216 is connected to the output axis of the stepping motor 215. A driving arm 217 in engagement with the screw shaft 216 is connected to the tip of a piston 218 of the syringe pump 214. At the same time the screw shaft 216 is rotated by means of the stepping motor 215, the piston 218 moves up and down. The syringe pump 214 is connected to the fluid manifold 213 by means of a solution sending tube 250 via connectors 219 and 220. The syringe pump 214 is also connected to a chamber 234 (see FIG. 13) containing liquid (cleaning liquid) filling the flow channel by means of a solution sending tube 220b via a connector 220a.

Figure 11:
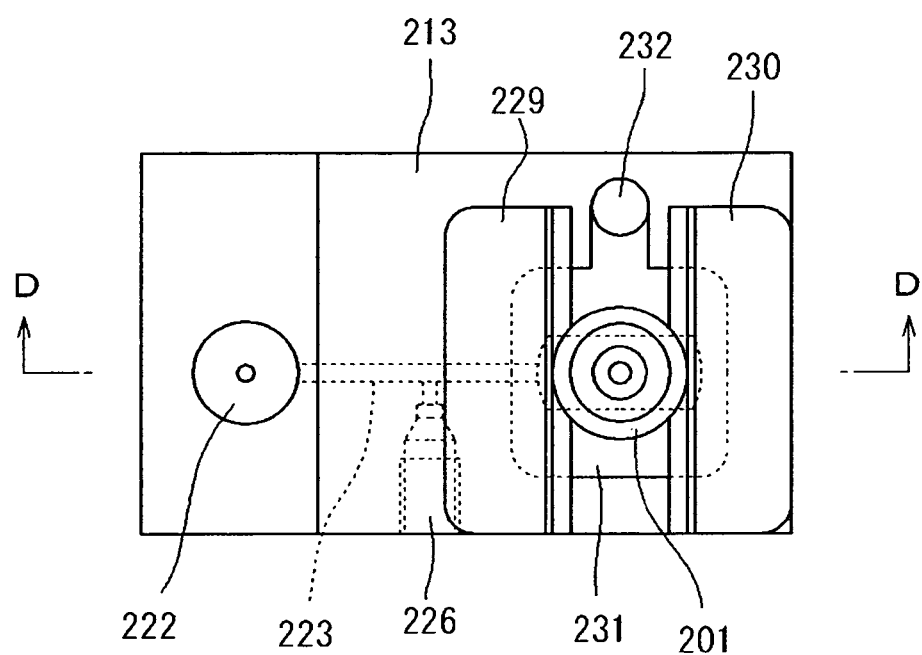
FIG. 11 is a top view of a fluid manifold of the sample preparation member shown in FIG. 10.
Figure 12:
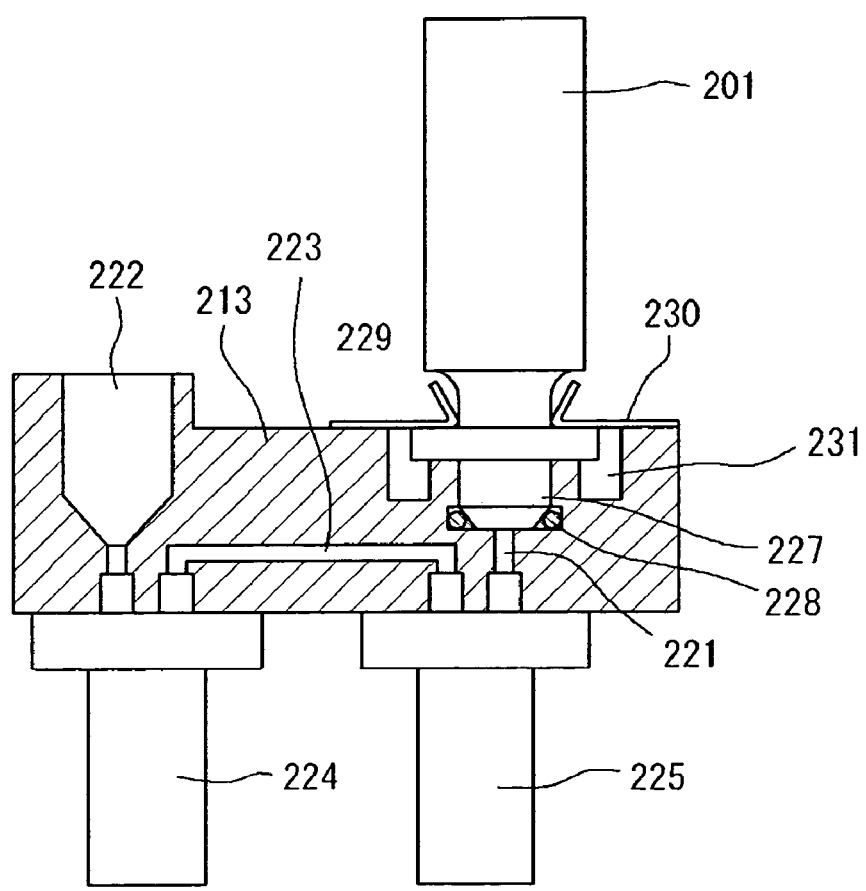
FIG. 12 is a sectional view taken in the direction of the arrows substantially along the line D-D of FIG. 11

As shown in FIGS. 11 to 12, the fluid manifold 213 has a column connection 221, to which the liquid introducing member 203 of the column 201, and a liquid sample receiving member 222 for receiving the liquid samples.

The fluid manifold 213 has the flow channel 223 therein and a electromagnetic valve 224 for opening and closing between the liquid sample receiving member 222 and the flow channel 223 and a electromagnetic valve 225 for opening and closing between the flow channel 223 and the column connection 221 at the bottom thereof. The fluid manifold 213 has connector holes 226 for the connectors for connecting the connectors 220 to the sides thereof, and this connector hole 226 is connected to the flow channel 223.

Figure 13:
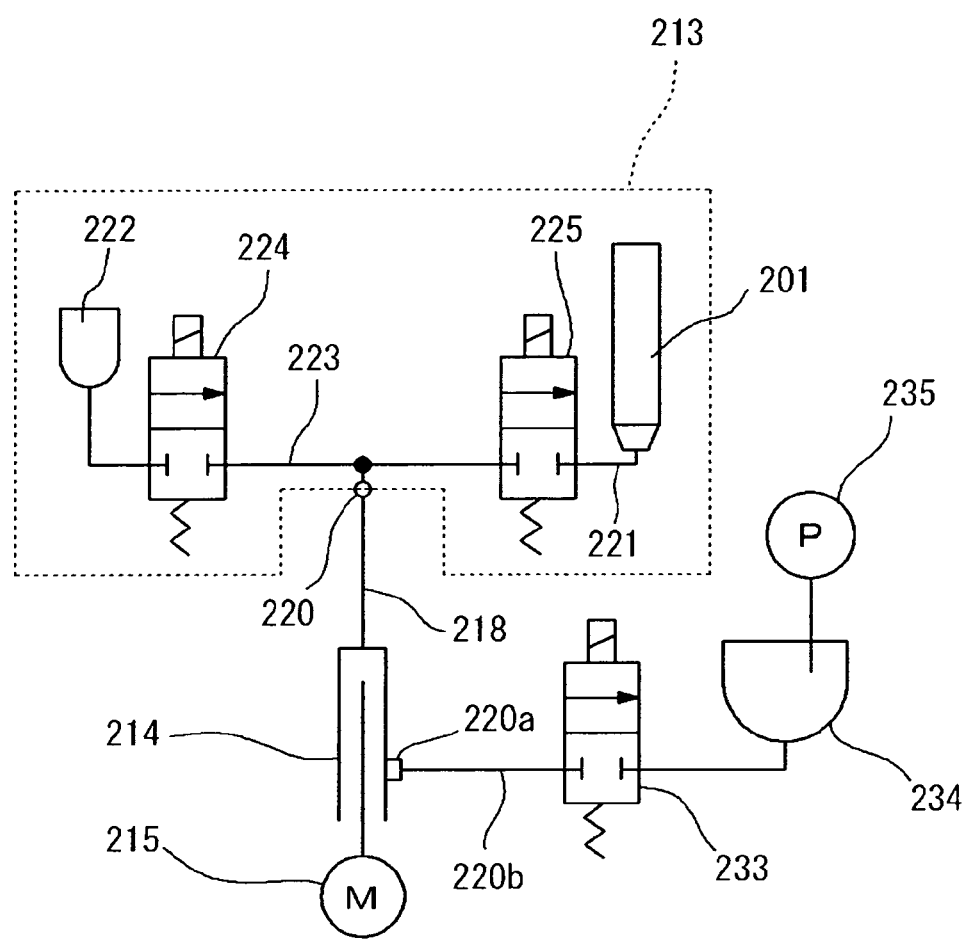
FIG. 13 is a fluid circuit view of the sample preparation member shown in FIG. 10.

FIG. 13 is a schematic view showing the circuit of the sample preparing member 211, along which the fluid flows. As shown in the figure, the syringe pump 204 is connected to the fluid manifold 213 vie the connectors 20. To the syringe pump 214, the chamber 234 is connected via the electromagnetic valve 233, a positive pressure being applied to the chamber 234 from a positive pressure source 235.

Now, a method for loading the column 201 into the fluid manifold 213 is described.

As shown in FIGS. 11 to 12, a column receiving pocket 227 for receiving the lower end of the column 201 is formed on the upper surface of the fluid manifold 213. The center of the bottom of the pocket 227 passes though the column connection and the O ring 228 is attached along the circumference at the bottom thereof. On the upper surface of the fluid manifold 213, two pressing plates 229 and 230 with L-shape cross sections are fixed in parallel, between which a space wider than the width W and narrower than D is left at the center of the column loading pocket 227.

Then, after the column 201 is loaded into the column loading pocket 227, the flange 209 is inserted passing through between the pressing plates 229 and 230, and then rotated clockwise or counterclockwise by 90 degrees. Thereby, the portion with D in diameter of the flange 209 is engaged with the pressing plates 229 and 230 and the flange 209 is fixed between the pressing plates 229 and 230 by means of flexibility exerted by the O ring 228. To remove the column 201, it may be rotated clockwise or counterclockwise by 90 while being held.

When the column 201 is loaded into the fluid manifold 213 of the sample preparing members 211, the pocket 227 of the fluid manifold 213 is filled with the fluid in order to prevent air bubble from entering and the fluid is flown out due to the volume of the column as soon as the tip of the column 201 is inserted into the pocket 227. To prevent the fluid from flowing out into the periphery, an overflow holding pocket 231 is formed around the column loading pocket 227 and at a point of the overflow holding pocket 231, an overflow discharging pocket 232 is formed for sucking the overflow using a pipette.

Various kinds of specimens and reagents are injected or sucked into or from their given places by means of a dispensing mechanism 3 equipped with the pipettes.

Now, the operation principle of the apparatus when specimens or reagents are injected into the liquid sample receiving member 222 is described. Once the specimens or reagents have been injected into the liquid sample receiving member 222, the electromagnetic valve 224 opens (the electromagnetic valves 225 and 233 close) and the syringe pump 214 starts its sucking operation. Thereby, the specimens and reagents are sucked on the side of syringe pump 214 passing through the electromagnetic valve 224. Next, the electromagnetic valve 224 closes, the electromagnetic valve 225 opens, and the syringe pump 214 discharges the specimens or reagents. Accordingly, the specimens or reagents pass through the electromagnetic valve 225 and sent into the column 201.

[Dispensing Mechanism]

As shown in FIG. 1, the dispensing mechanism 3 has a frame 352 for moving the pipette in the X direction, a frame 353 for moving the pipette in the Y direction, a plate 354 for moving the pipette in the Z direction.

The frame 352 has a screw shaft 355 for moving the plate 354 in the X direction indicated by an arrow, a guide bar 356 for sliding the plate 354 while holding, and the stepping motor 357 for rotating the screw shaft 355.

The frame 353 has a screw shaft 358 for moving the frame 352 in the Y direction indicated by an arrow, a guide bar 359 for sliding the frame 352 while holding, and a stepping motor 361 for rotating the screw shaft 358. The plate 354 has a screw shaft 367 for moving the arm 368 supporting a pipette 362 in the Z direction indicated by an arrow, guide bar for sliding the arm 368 while supporting, and a stepping motor 370 for rotating the screw shaft 367.

According to this embodiment, the dispensing mechanism 3 has a pair of pipettes 362 and thereby, the specimens or reagents may be injected into or sucked from two specimen vessels at the same time, achieving efficient measurement.

[Fluid Member]

As shown in FIG. 1, at the back of the apparatus body 20, the fluid member 9 is connected to the pipette 362, the pipette washing bath 8, and the sample preparing members 211 for controlling the fluid. As shown in FIG. 13, the fluid member 9 is composed of the electromagnetic valves 224 and 225 of the sample preparing members 211, the electromagnetic valve 233 for controlling the fluid when the fluid is filled in the syringe 214 from a cooling liquid chamber, an electromagnetic valve for controlling the fluid when the fluid is sucked or discharged by the pipette 362, the electromagnetic valve for controlling the fluid when the fluid discarded from pipette 362 in waste bath 7 is sucked, and an electromagnetic valve for controlling the fluid when the pipette 362 is washed in the pipette washing bath 8.

[Electronic Board]

At the back of the apparatus body 20, the electronic board 10 is mounted for supplying driving signals to the sample preparing members 211, the stepping motors 357, 361, and 370, the fluid member 9, and the like.

[Detecting Member]

The detecting member 4 measures the quantity of fluorescent material, which reflects the quantity of protein trapped by the porous membrane 122 of the chip 121 for protein immobilization and the quantity of fluorescent material, which reflects the quantity of the phosphate group. To measure these quantities, the detecting member 4 irradiates an excitation light onto the chip 121 for protein immobilization, detects the generated fluorescent, outputs to the electronic board 10 an electric signal with a strength corresponding to the intensity of the detected fluorescence. The detecting member 4 may use a system such as the commonly used light source, lighting system, and light-receiving system appropriately.

[Control Means]

Figure 14:
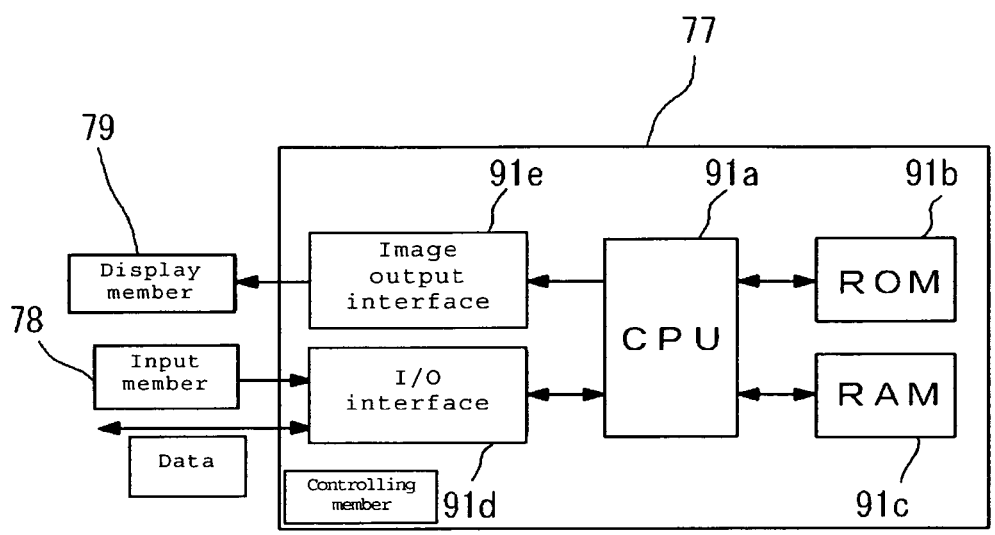
FIG. 14 is a block diagram showing hardware configuration of the control means.

As shown in FIG. 14, the personal computer 12 acting as a control means is composed of a controlling member 77 connected to the electronic board 10, an input member 78 for entering data in the controlling member 77, and a display member 79 for indicating the results of analysis and the like. The controlling member 77 configures an analytical means in the present invention, a first (second) activity value obtainer for obtaining the activity values from the fluorescence intensity using the analytical curve, and a first (second) expression level obtainer for obtaining the expression levels from the fluorescence intensity using the analytical curve.

As shown in FIG. 14, the controlling member 77 is composed of CPU91a, ROM91b, RAM91c, an I/O interface 91d, and an image output interface 91e. The ROM 91b contains an operating system, a control program for controlling the operation of apparatus, and data necessary in executing the control program. The CPU91a is capable of loading the control program into the RAM91c for execution or capable of directly executing it from the ROM91b. Data processed by the CPU91a this way is sent to the electronic board 10 via the I/O interface 91d and data necessary in processing by the CPU91a is received via the I/O interface 91d from the electronic board 10. The CPU91a may control the electronic board 10 by executing the control program. The CPU91a obtains the expression levels and activity values of the cyclin-dependent kinase based on the luminescence intensity obtained at the detecting member 4 and based on the obtained values, and acquires information on the characteristics of cells. To obtain the expression levels and activity values, the RAM91c stores the analytical curve, which is conversion data to be used in converting the fluorescence intensity into the expression levels or activity values.

Figure 15:
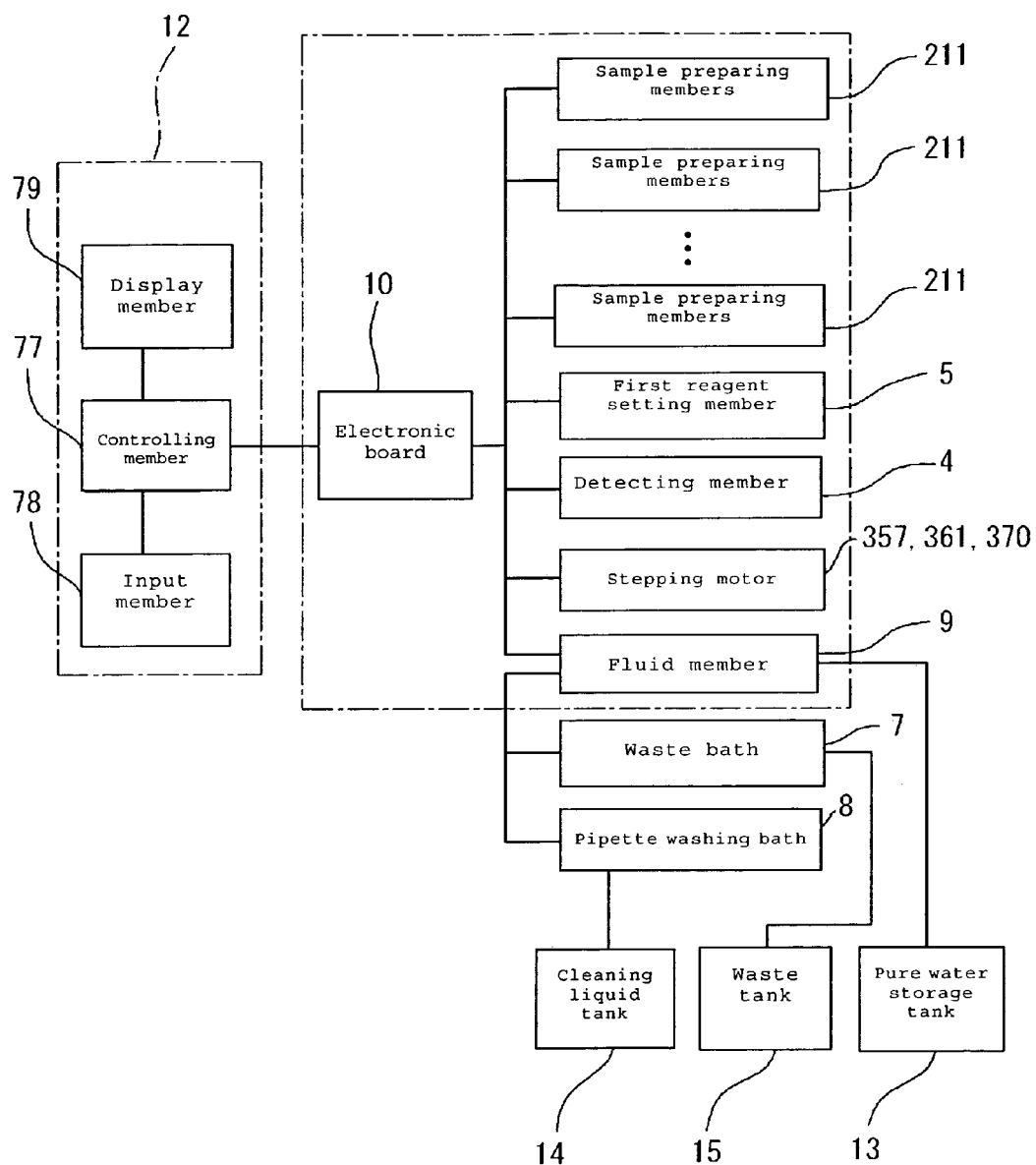
FIG. 15 is a block diagram showing a control system taking control of the determination apparatus.

FIG. 15 is a block diagram showing the control system for controlling the determination apparatus A of the present embodiment. As shown in the figure, the control system is composed of the electronic board 10 containing a driver circuit for driving the members of the dispensing mechanism 3 and the personal computer 12 containing the controlling member 77 for controlling the electronic board 10 and analyzing the results from the detecting member 4, an input member 78 for entering data and the like into the controlling member 77, and the display member 79 for indicating the analysis results analyzed at the control member 77.

The controlling member 77 outputs from the electronic board 10 the driving signal for driving the stepping motor 215 of the sample preparing members 211, the driving signal for controlling the temperature of the first reagent setting member 5, the driving signal for driving the stepping motor 357, 361 and 370, and the driving signal for driving the electromagnetic valve of the fluid member 9 by controlling the electronic board 10. The controlling member 77 receives the detected signals from the detecting member 4 via the electronic board 10.

Next, the method of determining the characteristics of the cells using the determination apparatus A according to this embodiment is described giving an example of the case where the malignancy levels (levels of recurrence risk) of human cancer cells and the effectiveness of (sensitivity to) the anticancer drugs are determined.

(1) Preprocessing by the Solubilization Apparatus

Prior to the processing by the determination apparatus A, the solubilization apparatus B is used to collect the liquid specimens from the tissues cut out from the patients. First, the specimens are put into the eppen tube using the tweezers. The eppen tube is set in the specimen setting member 33 of the solubilization apparatus B as shown in FIG. 1 and the start button of the operating member 31 is pressed. Then, the pestel 34 moves down to the given position and the tissue in the eppen tube is pressed against the bottom of the tube.

In this state, the solubilized liquid such as a buffer containing a surface active agent and a protease inhibitor is injected into the eppen tube automatically or manually. Then, the pestel 34 is rotated to grind the tissues. After a given time has passed, the moving pestel 34 is stopped and then moved up, and finally the eppen tube is taken off from the specimen setting member 33. Then, the content of the eppen tube is centrifuged and the obtained supernatant is collected manually as specimens.

(2) Setting the Specimens or the like on the Determination Apparatus

The supernatant liquid is put into two specimen vessels, diluted using different dilution rates, and the specimen vessels are set in the given position of the first reagent setting member 5. One of two specimens is used for expression level measurement and another is used for activity value measurement.

The chip 121 for protein immobilization is set in the chip setting member 1 and eight columns 201 are set the sample preparing members 211 of the activity measurement unit 2, respectively.

(3) Overall Flow of Process by the Determination Apparatus

Figure 17:
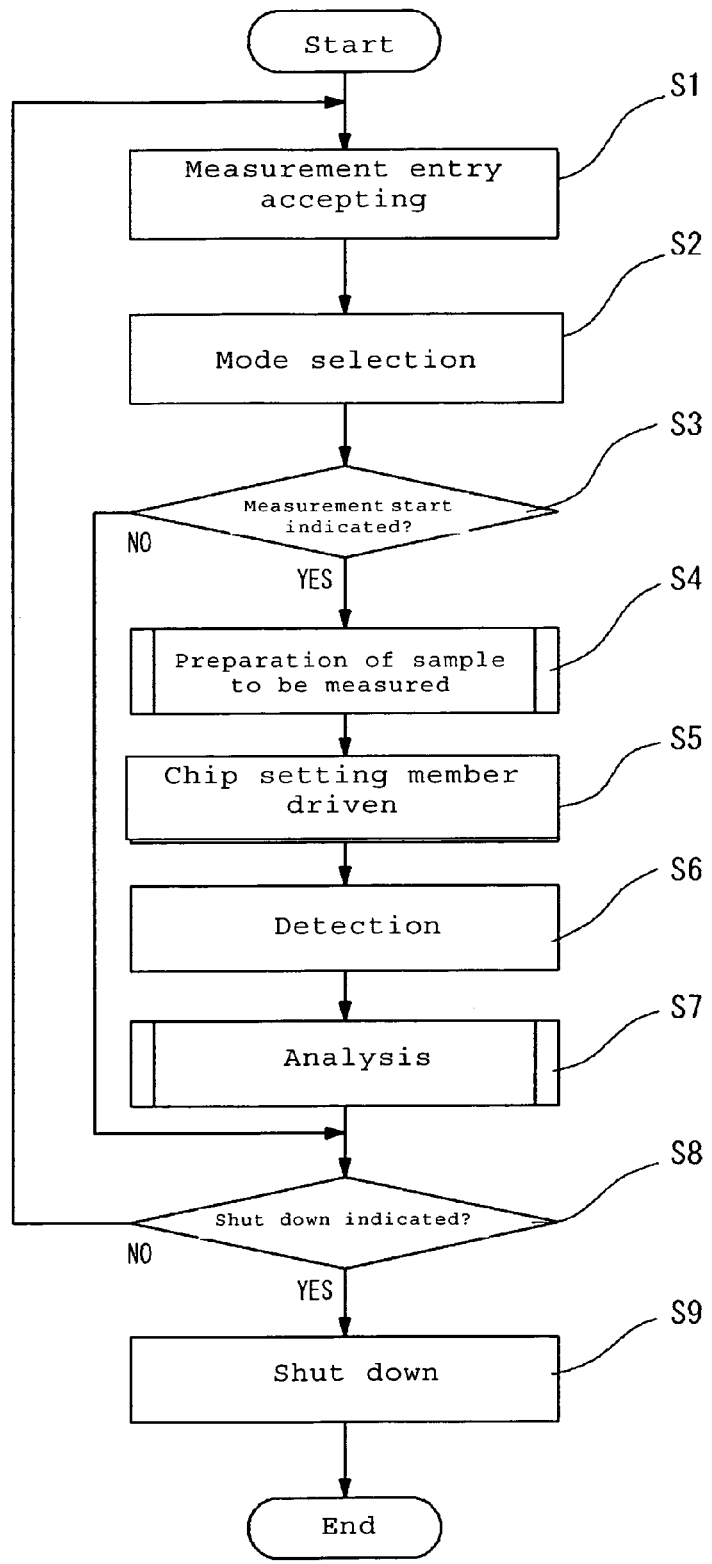
FIG. 17 is a view illustrating an overall process flow of the determination apparatus.

FIG. 17 shows the overall flow of the process by the determination apparatus. If no "Yes" or "No" is shown for the decision diamonds in the flow chart, the downward direction indicates "Yes" and the rightward (leftward) direction indicates "No". All the steps described below are controlled by the controlling member 77.

First, at power on, a step of accepting entries for measurement (step S1) is initiated. This step accepts entered data related to measurement such as specimen numbers. Second, a step of accepting the selection of either one of the measurement mode, the prognosis predicting mode (mode for determining the malignancy levels of the human cancer cells (levels of recurrence risk)) or the sensitivity to anticancer drugs mode (mode for determining the effectiveness of (sensitivity to the anticancer drugs)) is initiated (step S2). Specifically, in the display member 79 of the personal computer 12, two buttons for entering these modes. The operator clicks the entry button of the desired mode. In this example, the sensitivity to a taxane anticancer drug is determined in the sensitivity to anticancer drug mode. In addition to the two modes, the prognosis prediction—sensitivity to anticancer drugs mode may be selected.

Then, it is determined whether the indication of initiating the measurement has been accepted (step S3). If Yes, the operator proceeds to the step S4 while if No, proceeds to the step S8.

Next, the specimens are sucked from the specimen vessels set in the first reagent setting member 5 and samples are prepared by applying the given steps to the sucked specimens to prepare the samples for fluorescence detection (step S4). This step involves a sub-step of preparing the samples for expression level measurement and a sub-step of preparing the samples for activity value measurement, both of them being described in detail later. These two sub-steps are executed in parallel.

The chip setting member 1, on which the chip 121 for protein immobilization containing samples for fluorescence detection is set, is moved into the detecting member 4 from the position shown in FIG. 1 (step S5).

Then, an excitation light is irradiated onto the wells of the chip 121 for protein immobilization and fluorescence emitted from the samples for fluorescent detection is detected (step S6).

Next, at the controlling member 77 of the personal computer 12, the fluorescence intensity is obtained and the results of analysis are output based on the obtained fluorescence intensity (step S7).

It is determined whether the shout down indication for the determination apparatus has been received (step S8). If Yes, the operator proceeds to the step S9 while if No, returns to the step S1.

Finally, a step of shutting the apparatus down is executed and the power switch is turned OFF. (step S9).

(4) Preparing Samples for Expression Level Measurement

Figure 18:
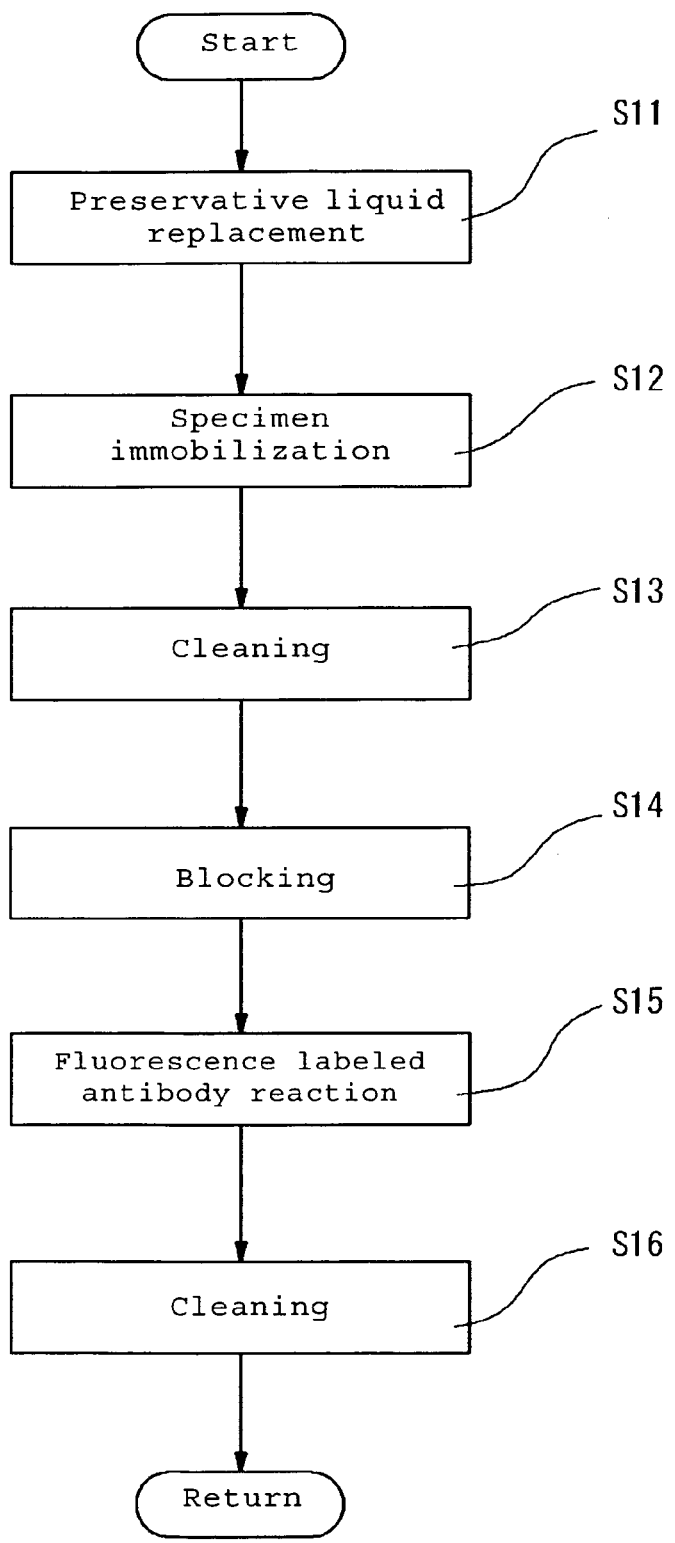
FIG. 18 is a view illustrating a process flow of preparing samples for expression level measurement.

FIG. 18 shows the flow of preparing the samples for expression level measurement in the step S4.

First, the preservative liquid previously stored in the wells of the chip for protein immobilization is discharged and the wells are cleaned (step S11). The wells are cleaned by injecting the cleaning liquid into the wells from the upper side with the pipette of the dispensing mechanism 3 and the injected cleaning liquid is sucked under the negative pressure from the lower side of the chip for protein immobilization through the porous membrane. The same steps should be followed for the cleaning steps described below.

Then, the specimens for expression level measurement are sucked out from the specimen vessels set in the first reagent setting member 5 using the pipette, the specimens are injected into a plurality of given wells, and then sucked from the under side of the chip for protein immobilization under the negative pressure. This immobilizes the protein on the porous membrane of the chip for protein immobilization (step S12).

In the same way as that of the step S11, the given wells are cleaned with a cleaning liquid. Accordingly, the components other than protein are removed from the porous membrane of the chip for protein immobilization (step S13).

Subsequently, a blocking liquid is injected into the given wells, the wells are left for 15 or more minutes (for example, 30 minutes) as they are, and the blocking liquid remaining in the wells is discharged (step S14). This prevents the CDK 1 antibody (fluorescence labeled CDK 1 antibody), the CDK 2 antibody (fluorescence labeled CDK 2 antibody), and p21 antibody (fluorescence labeled p21 antibody), all of which are fluorescence labeled, from immobilizing on the portions of the porous membrane with no protein immobilized. Any commercially available products may be used for the fluorescence labeled CDK 1 antibody, the fluorescence labeled CDK 2 antibody, and the fluorescence labeled p21 antibody.

Next, the fluorescence labeled CDK 1 antibody, the fluorescence labeled CDK 2 antibody, and the fluorescence labeled p21 antibody are injected into the given wells. Each of fluorescence labeled antibodies is injected into two wells. 20 to 30 minutes after, once the reaction between the fluorescence labeled antibodies and the protein (CDK1, CDK2, or p21) immobilized on the porous membrane has been finished, the injected fluorescence labels are discharged (step S15).

Finally, in the same way as that of step S13, the given wells are cleaned with the cleaning liquid (step S16).

(5) Preparing the Samples for Activity Value Measurement

Figure 19:
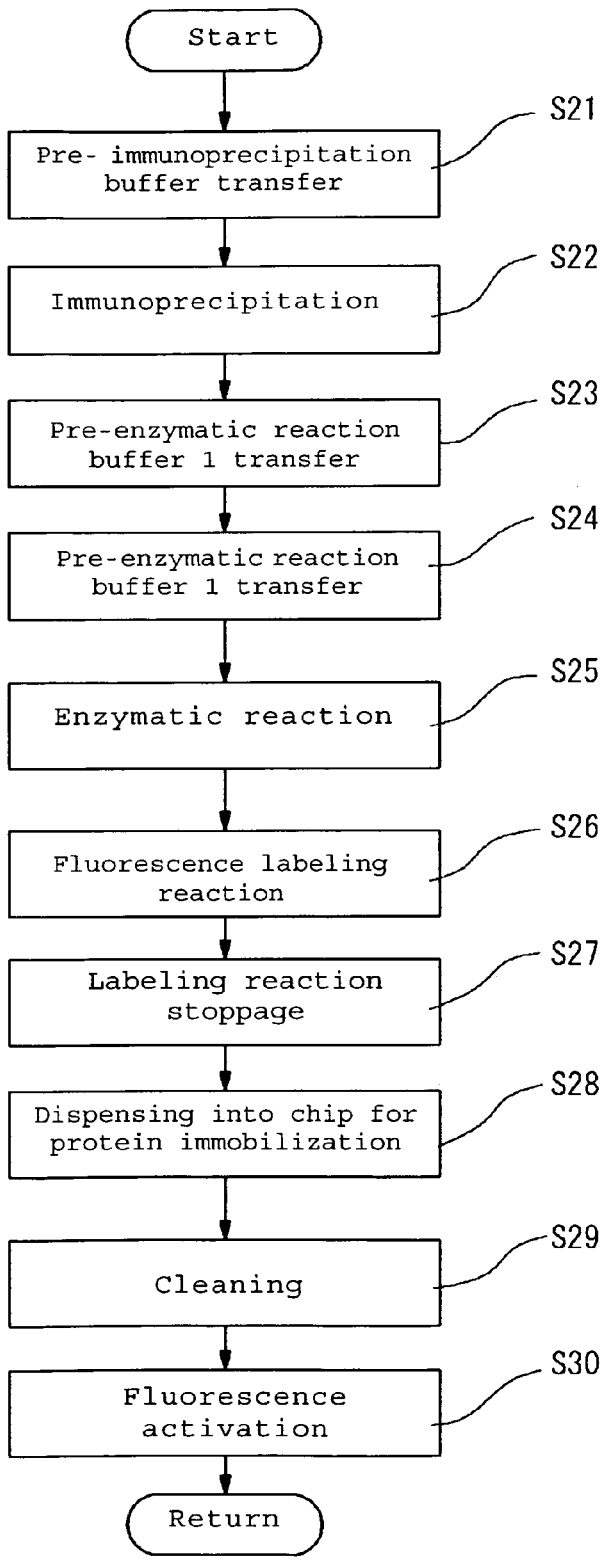
FIG. 19 is a view illustrating a process flow of preparing samples for activity value measurement.

FIG. 19 shows the flow of preparing the samples for activity value measurement in the step S4. In the step of preparing the samples for activity value measurement, four sample preparing members 211 disposed on the near side in the figure and four sample preparing members 211 also disposed on the far side in the figure are used as activity measurement unit 2. It is assumed that the sample preparing members 211 of the activity measurement unit 2 are called a first sample preparing member (Ac1), a second sample preparing member (Ac2), a third sample preparing member (Ac3), and a fourth sample preparing member (Ac4), respectively from the leftmost one on the far side in the figure and called a fifth sample preparing member (Ac5), a sixth sample preparing member (Ac6), a seventh sample preparing member (Ac7), and an eighth sample preparing member (Ac8), respectively from the leftmost on the near side in the figure.

First, a buffer, which is a reagent for cleaning, is injected into the liquid sample receiving member 222 for each of the first to eighth sample preparing members (Ac1 to Ac8) using the pipette in the dispensing mechanism 3. The syringe pump 214, the electromagnetic valves 224 and 225 operate for each of the first to eighth sample preparing members (Ac1 to Ac8) as described before to send the buffer into the column 201. Any excess buffer in all the columns 201 is discarded by sucking using the pipette of the dispensing mechanism 3 (step S21).

Figure 20:
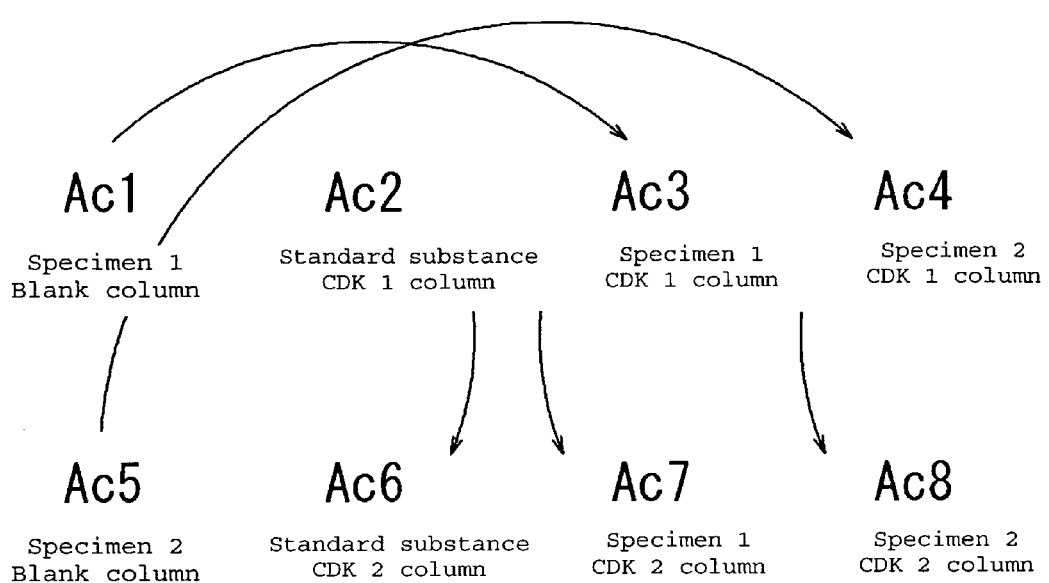
FIG. 20 is a view explaining an example of using reagents or the like with the measurement method of the present invention.

Next, immunoprecipitation (the reaction between the antibodies and the CDKs) is performed (step S22). First, the specimen 1 for activity value measurement is sucked from one specimen vessel set on the first reagent setting member 5 using one pipette and the specimen 2 for activity value measurement using another pipette. The specimen 1 for activity value measurement sucked from the specimen vessel is injected into the liquid sample receiving member 222 of the first sample preparing member (Ac1) as shown in FIG. 20. The specimen 1 is sent into the column 201 of the first sample preparing member (Ac1) by means of the operating syringe pump 214, electromagnetic valves 224 and 225 as described above. At that time, as the piston 218 reciprocates up and down by 1.5 times (discharge-suction-discharge), the specimen 1 also reciprocates the carrier support 206 in the column 201 by 1.5 times. On the other hand, the specimen 2 for activity value measurement sucked from the specimen vessels are first injected into the liquid sample receiving member 222 of the fifth sample preparing member (Ac5). Then, the specimen 2 is sent to the column 201 of the fifth sample preparing member (Ac5) in the same way described above. On the carrier supports 206 in the columns 201 of the first sample preparing member (Ac1) and the fifth sample preparing member (Ac5), no CDK 1 or CDK 2 antibody was immobilized. Accordingly, in the first sample preparing member (Ac1) and the fifth sample preparing member (Ac5), no CDK 1 or CDK2 is immobilized and in the columns 201 of the first sample preparing member (Ac1), the specimens 1 containing CDK1 and CDK2 are stored and in the columns 201 of the fifth sample preparing member (Ac5), the specimens 2 containing CDK 1 and CDK 2 are stored. Next, the specimens 1 stored in the columns 201 of the first sample preparing member (Ac1) are sucked using the pipettes and injected into the liquid sample receiving member 222 of the third sample preparing member (Ac3). Then, the specimens 1 are sent to the columns 201 of the third sample preparing member (Ac3) in the same way as that mentioned above. On the other hand, the specimens 2 stored in the columns 201 of the fifth sample preparing member (Ac5) are sucked using the pipettes and injected into the liquid sample receiving member 222 of the fourth sample preparing member (Ac4). Then, the specimens 2 are sent to the columns 201 of the fourth sample preparing member (Ac4) in the same way as that mentioned above. In the carrier supports 206 in the columns 201 of the third sample preparing member (Ac3) and the fourth sample preparing member (Ac4), the CDK 1 antibody has been immobilized. Accordingly, CDK 1 is immobilized, but CDK 2 is not, in the third sample preparing member (Ac3) and the fourth sample preparing member (Ac4). In the columns 201 of the third sample preparing member (Ac3), the specimens 1 containing CDK 2 but no CDK 1 are stored, and in the columns 201 of the fourth sample preparing member (Ac4), the specimen 2 containing CDK 2 but no CDK 1 are stored.

Next, the specimens 1 stored in the columns 201 of the third sample preparing member (Ac3) are sucked using the pipettes and injected into the liquid sample receiving member 222 of the seventh sample preparing member (Ac7). Then, the specimens 1 are sent to the columns 201 of the seventh sample preparing member (Ac7) in the same way as that described above. On the other hand, the specimens 2 stored in the columns 201 of the fourth sample preparing member (Ac4) are sucked using the pipettes and injected into the liquid sample receiving member 222 of the eighth sample preparing member (Ac8). Then, the specimens 2 are sent to the columns 201 of the eighth sample preparing member (Ac8) in the same way as that described above. In the carrier supports 206 of the column for the seventh sample preparing member (Ac7) and the eighth sample preparing member (Ac8), the CDK 2 antibody has been immobilized. Accordingly, in the seventh sample preparing member (Ac7) and the eighth sample preparing member (Ac8), CDK 2 is immobilized. For this reason, in the columns 201 of the seventh sample preparing member (Ac7), the specimens 1 containing no CDK 1 and CDK 2 are stored and in the columns 201 of the eighth sample preparing member (Ac8), the specimens 2 containing no CDK 1 and CDK 2 are stored. The specimens 1 and 2 stored in the columns 201 of the seventh sample preparing member (Ac7) and the eighth sample preparing member (Ac8) are sucked using the pipettes and discarded into the waste bath 7.

The first sample preparing member (Ac1) and the fifth sample preparing member (Ac5) are used for background activity measurement, the third sample preparing member (Ac3) and the fourth sample preparing member (Ac4) are used for CDK1 activity measurement, and the seventh sample preparing member (Ac7) and the eighth sample preparing member (Ac8) are used for CDK 2 activity measurement.

Thus, by injecting the remaining specimens in the columns into other columns, background measurement and CDK 1 and CDK 2 activity measurement may be achieved even on a small amount of specimens.

Then, to wash away unwanted components from the specimens for removal, the buffer 1 is sent to the columns 201 (step S23).

Subsequently, as the buffer 1 affects the enzymatic reactions performed in the step S25, the buffer 2 is sent to the columns 201 for washing away the components of the buffer 1 mainly to establish the conditions suitable for these enzymatic reactions (step S24).

Next, a substrate reaction solution containing substrates HistonH1 and ATPγs is injected into the columns 201 and the piston 219 is reciprocated by 5.5 times (step S25). The liquid pressed into the columns 201 from the lower side thereof is stored as it is. This step introduces a phosphate group into HistonH1 using CDK 1 or CDK 2 as an enzyme. The quantity of the phosphate group is governed by the activity value of CDK1 or CDK 2 as an enzyme. Accordingly, by measuring the quantity of the phosphate group, the activity value of CDK 1 or CDK 2 may be obtained. The background activity values obtained using the first sample preparing member (Ac1) and the fifth sample preparing member (Ac5), shown in FIG. 20, are used for background correction as described later.

Subsequently, the fluorescence labeled reagent is dispensed directly into the columns 201 from the upper side thereof using the pipettes to bind the fluorescence label to the phosphate group introduced into HistonH1 (step S26). At that time, the pipettes repeatedly suck and discharge the liquid in the columns 201 for a given time for stirring.

After a given time (for example, 20 minutes) after the initiation of the step S26 has passed, the stop reagent is dispensed directly into the columns 201 in the same way as that of the fluorescence labeled reagent. In the same way as that of the Step 26, the pipettes repeatedly suck and discharge the liquid in the columns 201 for the given time for stirring (step S27). This stops binding of the phosphate group to the fluorescence label.

Then, the liquid in the columns 201 of the first sample preparing member (Ac1), the third sample preparing member (Ac3), the fourth sample preparing member (Ac4), the fifth sample preparing member (Ac5), the seventh sample preparing member (Ac7), and the eighth sample preparing member (Ac8) is dispensed into the six wells of the chip 121 for protein immobilization and then, the chip 121 for protein immobilization is sucked from the lower side thereof (step S28). This immobilizes HistonH1 protein containing the phosphate group, to which the fluorescence label has bound, on the porous membrane of the chip 121 for protein immobilization.

Next, the wells are cleaned in the same way as that of the step S11 in the process of preparing the samples for expression level measurement (step S29).

Finally, to activate fluorescence, the fluorescence enhancing reagent is dispensed into the wells and discharged six times (step S30).

(6) Analysis

Figure 21:
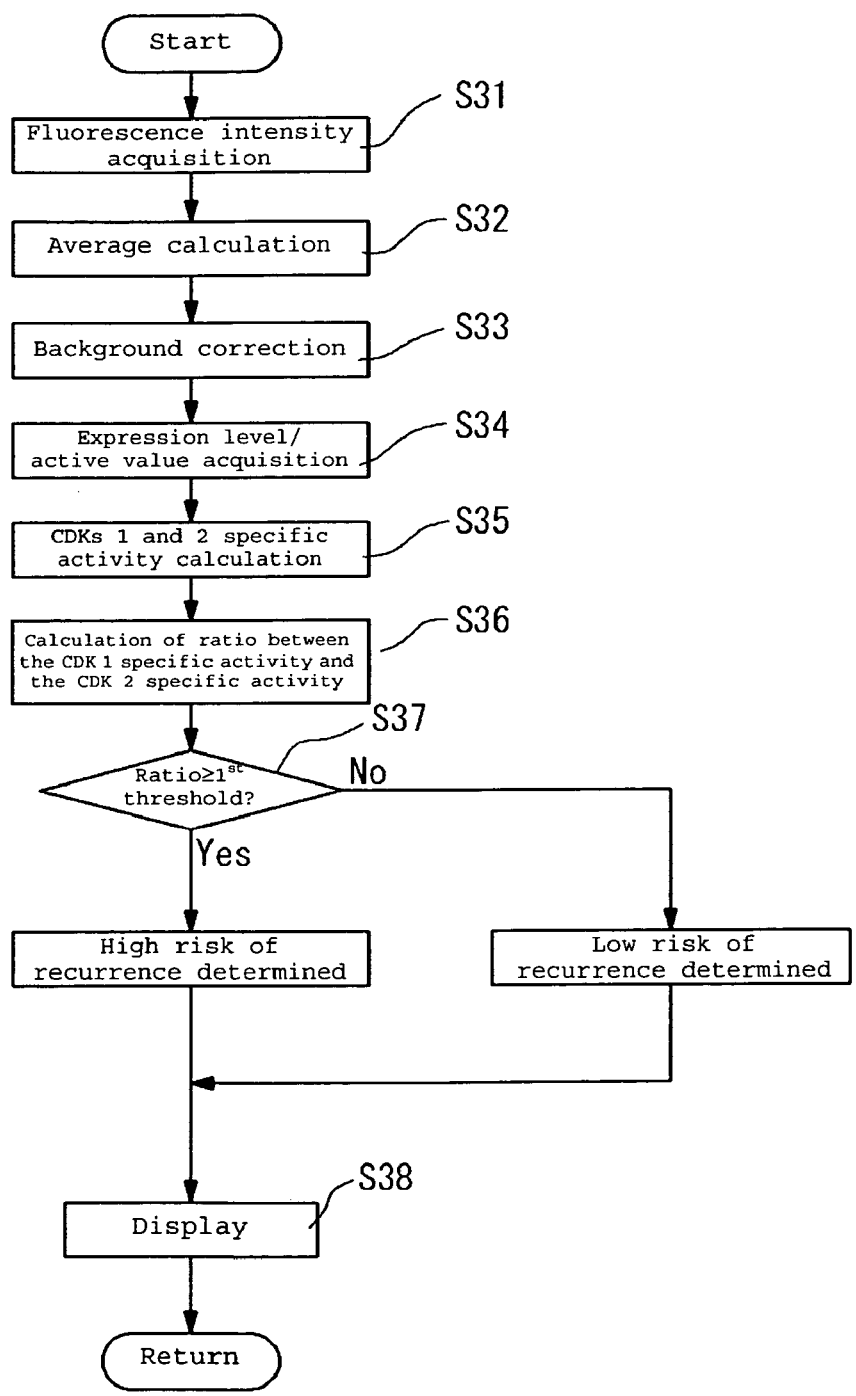
FIG. 21 is a view showing an overall flow of an example of the analysis process by the determination apparatus.

As shown in FIG. 21, the fluorescence intensity obtained at the detecting member is analyzed and the results of the analysis are output.

The controlling member 77 obtains two values for the fluorescence intensities for CDK 1 activity, CDK 1 expression, CDK 2 activity, CDK 2 expression, p21 expression, background activity, and background expression from the light receiving system of the detecting member 4 via the electronic board 10 (step S31).

Subsequently, the controlling member 77 calculates the average of obtained fluorescence intensities, two values for each item to be measured (step S32).

Next, the background activity value (average) is subtracted from the fluorescence intensity for CDK 1 activity (average), the background activity value (average) is also subtracted from and the fluorescence intensity for CDK 2 activity, for background correction for CDK 1 and CDK 2 activities. The background correction is made for the CDK 1 expression, CDK 2 expression, and p21 expression in the same way as that described above (step S33).

Subsequently, the expression levels and the activity values for each item are obtained using the analytical curves (step S34). The analytical curves are data used in converting the fluorescence intensities into the expression levels and activity values. They have been previously drawn using two or more kinds of specimens, of which the expression level or the activity value is known, when the lot of the reagent was changed, and stored in RAM91c of the controlling member 77.

Next, following the expressions below, the CDK 1 and CDK 2 specific activity values are calculated (step S35).

*CDK* 1 specific activity=*CDK* 1 activity value/*CDK* 1 expression level

*CDK* 2 specific activity=*CDK* 2 activity value/*CDK* 2 expression level

Following the expressions below, the ratio between the CDK 1 specific activity and the CDK 2 specific activity value is calculated (step S36).

Ratio between *CDK* 1 specific activity and *CDK* 2 specific activity=*CDK* 2 specific activity/*CDK* 1 specific activity Then, it is determined whether the ratio between the CDK 1 specific activity and the CDK 2 specific activity is at the first threshold or higher (step S37). If the ratio between the CDK 1 specific activity and the CDK 2 specific activity is at the first threshold or higher, the risk of cancer recurrence is determined to be higher and if it is lower, the risk is determined to be lower.

The CDK 1 expression levels, activity values, specific activity values, the CDK 2 expression levels, activity values, specific activity values, and the ratio between the CDK 1 specific activity and the CDK 2 specific activity, all of which offer the basis for determination of recurrence risk levels, are indicated together with the results of determining the recurrence risk levels (step S38).

Figure 22:
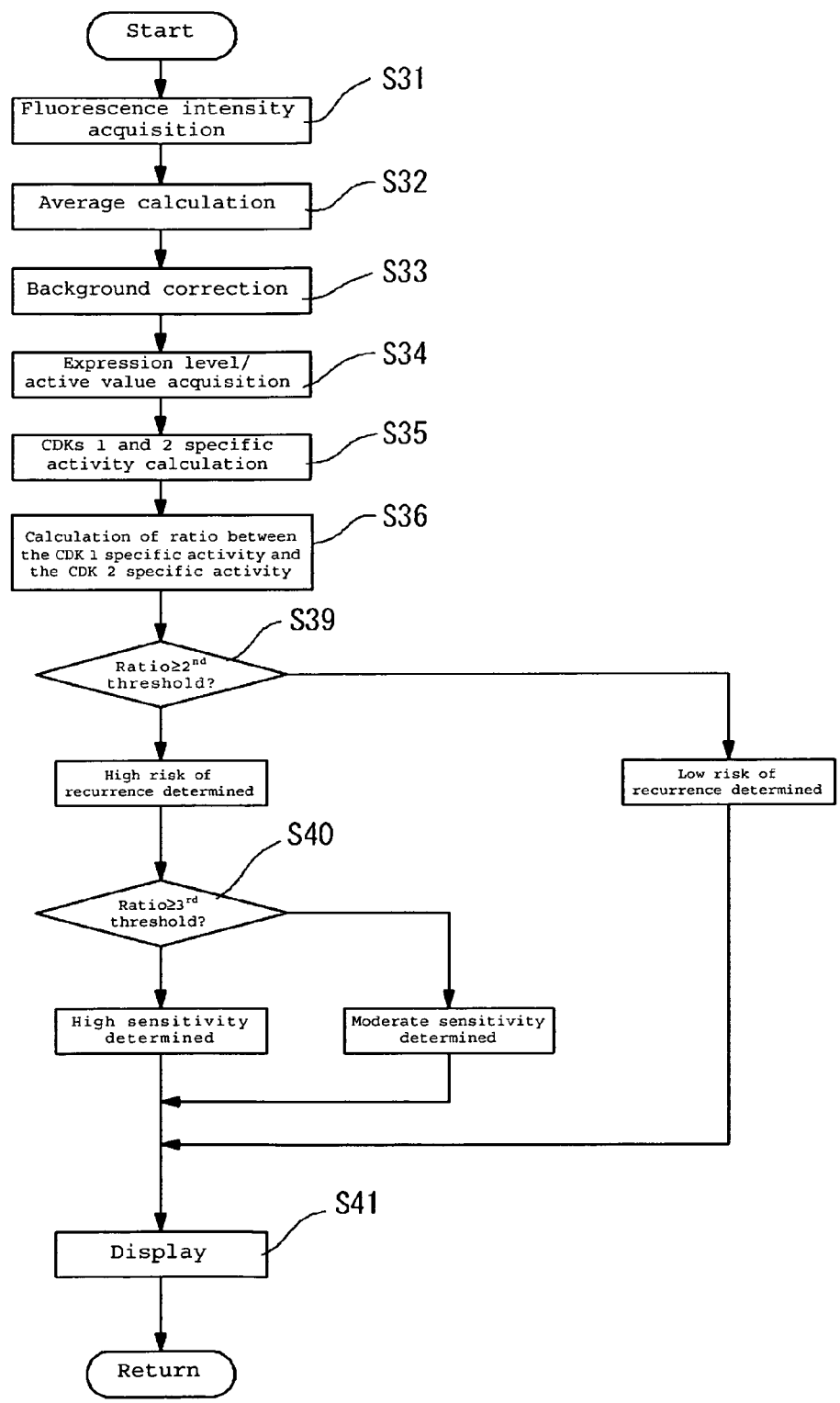
FIG. 22 is a view showing an overall flow of another example of the analysis process by the determination apparatus.

FIG. 22 shows the flow of the other implementation example of the analytical process shown in FIG. 21. In this example, the sensitivity to the taxane anticancer drug is determined.

The steps S31 to S36 of the analytical process shown in this implementation example are identical to those of the analytical process shown in FIG. 21.

Then, it is determined whether the ratio between the CDK 1 specific activity and the CDK 2 specific activity is at the second threshold or higher (step S39). If the ratio between the CDK 1 specific activity and the CDK 2 specific activity is at the second threshold or higher, the risk of cancer recurrence is determined to be higher and if the ratio is lower than the second threshold, the risk is determined to be lower.

If the ratio between the CDK 1 specific activity and the CDK 2 specific activity is higher the second threshold, it is determined whether the ratio between the CDK 1 specific activity and the CDK 2 specific activity is at the third threshold or higher (step S40). If the ratio between the CDK 1 specific activity and the CDK 2 specific activity is at the third threshold or higher, the sensitivity to the anticancer drug is determined to be higher, namely the anticancer drug is determined to be effective. If the ratio is lower than the third threshold, the sensitivity to the anticancer drug is determined to be moderate. For the third threshold, a larger value than the second threshold is used. For the second threshold, the same value as that of the first threshold is preferably used.

The CDK 1 expression levels, activity values, specific activity values, the CDK 2 expression levels, activity values, specific activity values, and the ratio between the CDK 1 specific activity and the CDK 2 specific activity, all of which offer the basis for each determination, are indicated together with the results of determining the recurrence risk levels or the result of sensitivity determination (step S41). For the results of determination, for example three types may be indicated; "low risk of recurrence", "high risk of recurrence, high sensitivity to anticancer drug", and "high risk of recurrence, moderate sensitivity to anticancer drug".

(7) Examples of Using the Results of Determination

Figure 23:
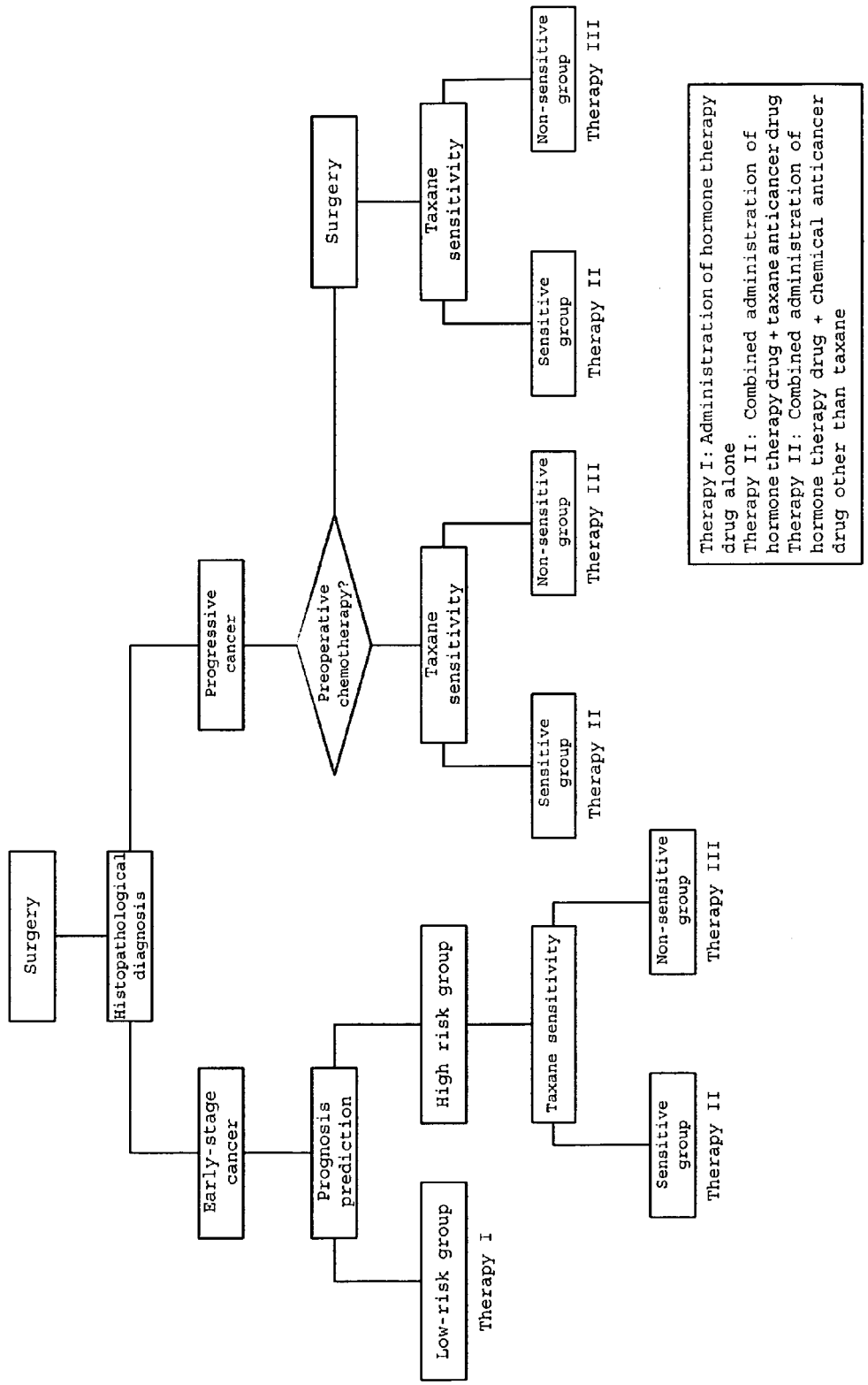
FIG. 23 is a view of an example of using the determination results obtained by the measurement method of the present invention.

FIG. 23 shows an example of using the results of determination by a doctor indicated in the step S41 shown in FIG. 22.

The possibility of breast cancer is confirmed in image diagnosis on the patients and biopsy is further done for histopatholigical or cytological diagnosis. If the result of histopathological diagnosis indicates early stage cancer, the cancer tissues are removed and the characteristics of the sample of the tissue are determined on the determination apparatus A. If the result of determination of tissue characteristics on the determination apparatus A indicates that the cancer is classified into a low risk group (the determination result "low risk of recurrence" is indicated on the determination apparatus A), a doctor selects Therapy 1 (administration of hormone therapy drug alone). If the result indicates that the cancer is classified into a Taxane sensitivity group, for which taxane anticancer drugs are effective (the determination result "high risk of recurrence, high sensitivity to anticancer drugs" is indicated on the determination apparatus A), the doctor selects Therapy 2 (combined administration of a hormone therapy drug and a taxane anticancer drug) or Therapy 3 (combined administration of a hormone therapy drug and a anticancer drug other than taxane).

When the result of histopathological diagnosis indicates that the cancer is classified into a group of progressive cancers, a discussion is made between the doctor and the patient about whether pre-operative chemotherapy (chemotherapy prior to extirpative surgery) would be applied. If pre-operative chemotherapy is applied, the sensitivity of biopsy samples, which have been immersed in anticancer (taxane) solution for 24 hours, to the anticancer drug is determined on the determination apparatus A. If the determination result "high sensitivity to an anticancer drug" is indicated on the determination apparatus A, Therapy 2 (combined administration of a hormone therapy drug and a taxane anticancer drug) is selected. It should be noted that if the determination result "moderate sensitivity to an anticancer drug" is indicated on the determination apparatus A, the taxane anticancer drugs are not always effective. For this reason, the doctor selects Therapy 2 (combined administration of a hormone therapy drug and a taxane anticancer drug) or Therapy 3 (combined administration of a hormone therapy drug and an anticancer drug other than taxane) at his/her discretion. This type of pre-operative chemotherapy enables the cancer tissues to be removed out after being reduced in size using the anticancer drug.

If no pre-operative chemotherapy is applied, extirpative surgery is done. The sensitivity of the sample of the cancer tissue collected to the anticancer drugs is determined on the determination apparatus A. If the determination result "high sensitivity to an anticancer drug" is indicated on the determination apparatus A, Therapy 2 (combined administration of a hormone therapy drug and a taxane anticancer drug) is selected. If the determination result "moderate sensitivity to an anticancer drug" is indicated on the determination apparatus A, the taxane anticancer drugs are not always effective. For this reason, the doctor selects Therapy 2 (combined administration of a hormone therapy drug and a taxane anticancer drug) or Therapy 3 (combined administration of a hormone therapy drug and an anticancer drug other than taxane) at his/her discretion.

Figure 24:
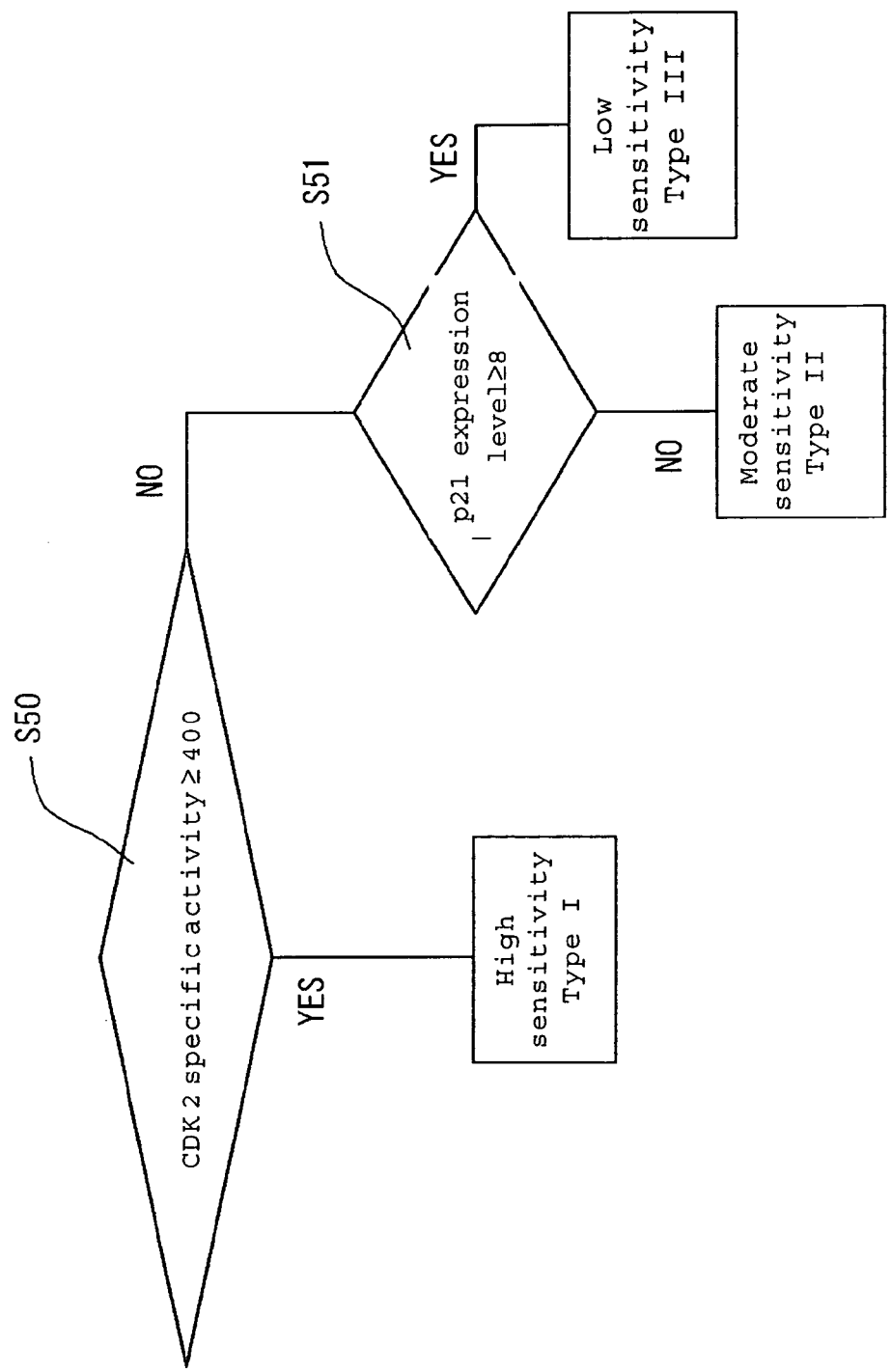
FIG. 24 is a view showing another implementation example of sensitivity analysis.

FIG. 24 shows another implementation example of sensitivity analysis. According to this example, the sensitivity of the tissue to the taxane anticancer drugs is also determined. The CDK 2 specific activity is compared with the threshold "400" (step S50). If the CDK 2 specific activity is at 400 or higher, the sensitivity of the tissue is determined to be high (Type I). If the CDK 2 specific activity is lower than 400, the p21 expression level is further compared with the threshold "8" (step S51). If the p21 expression level is at 8 or higher, the sensitivity of the tissue is determined to be low (Type III). If the p21 expression level is lower than 8, the sensitivity of the tissue is determined to be moderate (Type II). According to this implementation example, the thresholds for the CDK 2 specific activity and the p21 expression level may be set based on the pre-stored patient data.

Figure 25:
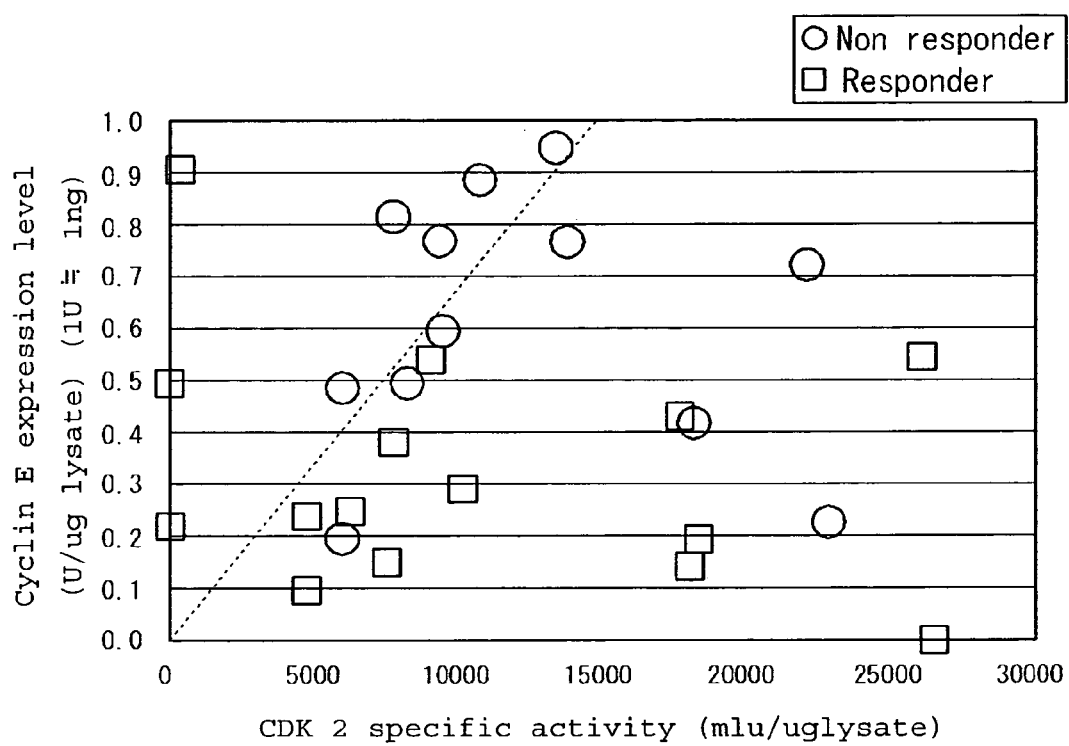
FIG. 25 is a view of an additional implementation example of sensitivity analysis.

FIG. 25 shows the other implementation example of sensitivity analysis. According to this implementation example, the sensitivity of the tissue to CE (anticancer drug) is determined based on the cyclin E expression level and the CDK 2 specific activity. Specifically, the ratio between the CDK 2 specific activity and the cyclin E expression level is compared with the given threshold to determine the sensitivity to CE (anticancer drug). The cyclin E expression level may be measured in the same way as that of the CDK 1 expression level by varying the reagent appropriately.

Figure 26:
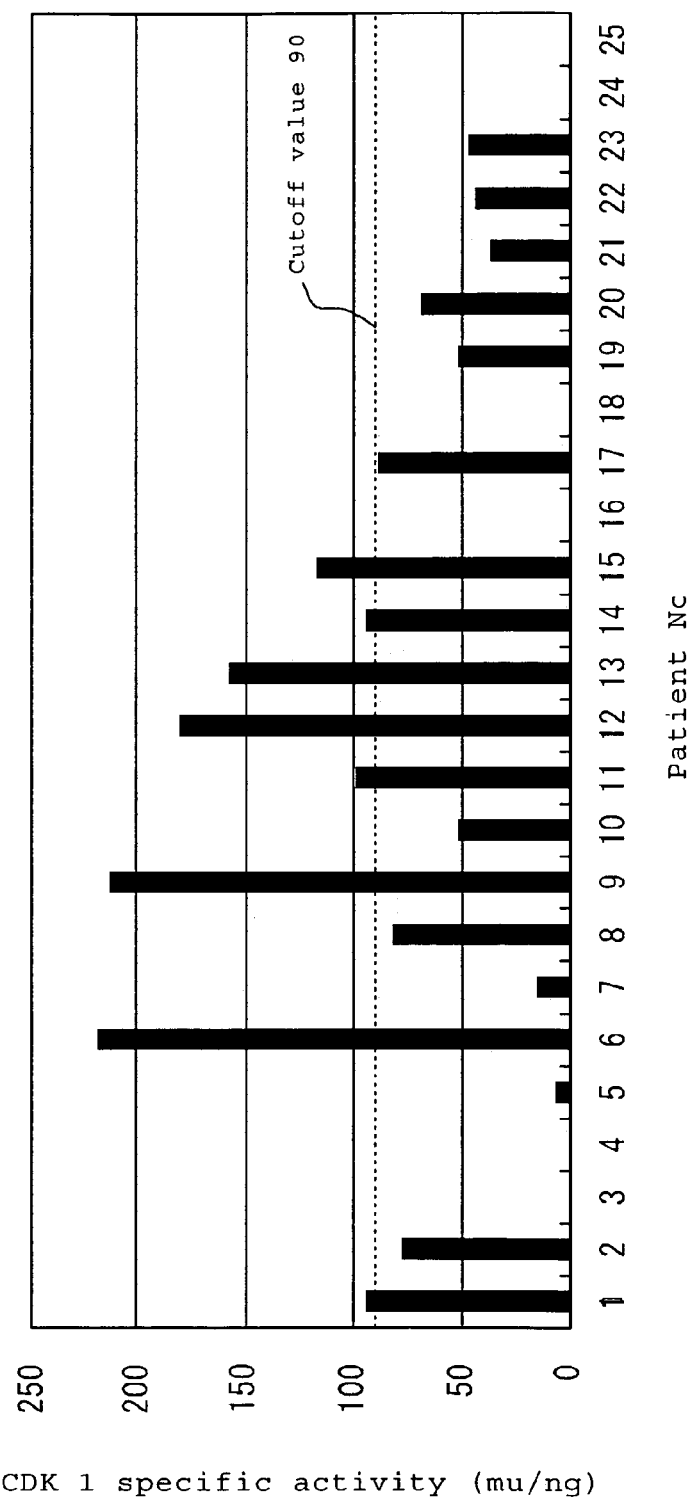
FIG. 26 is a view of a further implementation example of sensitivity analysis.

FIG. 26 shows further another implementation example of sensitivity analysis. According to this implementation example, the CDK 1 specific activity is compared with the given threshold to determine the sensitivity of the tissue to CMF (anticancer drug). According to this example, patients Nos. 1 to 16 are those, in whom no recurrence of cancer was observed after CMF (anticancer drug) had been continuously administered since extirpative surgery. The patients Nos. 17 to 25 are those, in whom cancer recurred even after CMF (anticancer drug) had been administered. In this case, if "90" is set for the threshold (cutoff value), no recurrence of cancer was not observed in eight cases (Nos. 1, 6, 9, 11 to 15) with their CDK 1 activity at 90 or higher. This suggests the threshold "90" is correct. To determine the sensitivity to the drugs, the tissues cryonically-preserved after being removed out were used.

Figure 27:
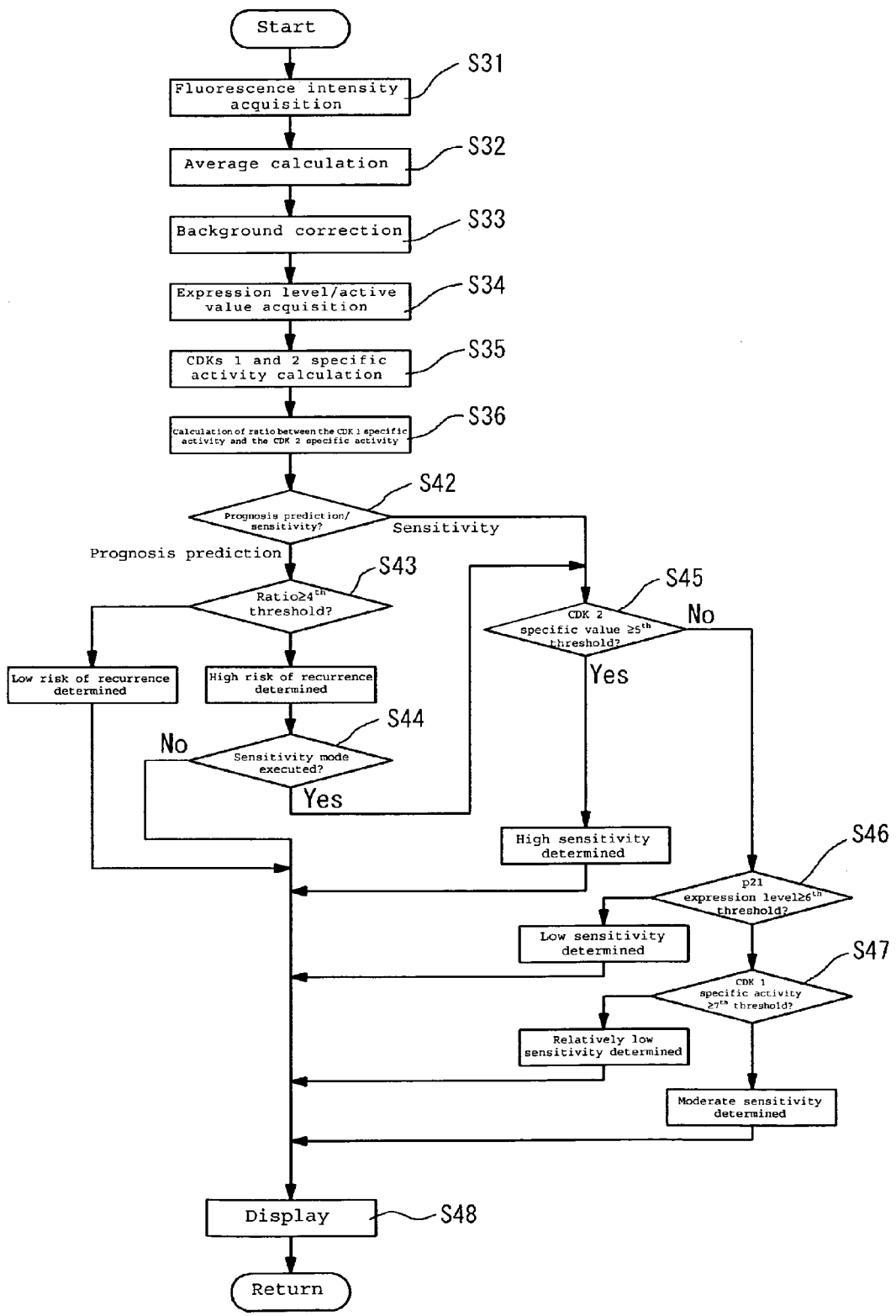
FIG. 27 is a view showing an overall flow of another example of the analysis process by the determination apparatus.

FIG. 27 shows a flow of other implementation example of analytical process indicated in FIG. 21. The steps S31 to S36 of the analytical process according to this implementation example is identical to those of the analytical process shown in FIG. 21. In the analytical process according to this implementation example, it is determined in the step S42 that the mode selected in the step S2 is the prognosis or sensitivity mode. If it is the prognosis mode, it is determined that the ratio between the CDK 1 specific activity and the CDK 2 specific activity is at the fourth threshold or higher (step S43). If it is the sensitivity mode, it is determined that the CDK 2 specific activity is at the fifth threshold or higher (step S45). In the step S43, if the ratio between the CDK 1 specific activity and the CDK 2 specific activity is at the fourth threshold or higher, the risk of recurrence is determined to be high. If the ratio is lower than the fourth threshold, the risk of recurrence is determined to be low.

If the risk of recurrence is determined high, the step of determining whether the sensitivity mode is selected is executed (step S44). Specifically, the bottoms for specifying whether the sensitivity mode is executed or only the results of determination of recurrence risk are indicated appear on the display member 79 of the personal computer 12. The step of accepting data entered by the operator is executed. In the step S44, if it is determined that the sensitivity mode is executed, the process proceeds to the step S45, and if it is determined that the sensitivity mode is not executed (that is, only the results of determination of recurrence risk are indicated) the process proceeds to the step S48. In the step S45, if the CDK 2 specific activity is at the fifth threshold or higher, the sensitivity is determined to high, namely the anticancer drug is effective. If the CDK 2 specific activity is lower than the fifth threshold, the p21 expression level is compared with the sixth threshold (step S46).

If the p21 expression level is lower than the sixth threshold, the sensitivity is determined to be lower. If p21 expression level is at the sixth threshold or higher, the CDK 1 specific activity is compares with the seventh threshold (step S47). If the CDK 1 specific activity is lower than the seventh threshold, the sensitivity is determined to be relatively lower. If the CDK 1 specific activity is at the seventh threshold or higher, the sensitivity is determined to be moderate.

The CDK 1 expression levels, activity values, specific activity values, the CDK 2 expression levels, activity values, specific activity values, the ratio between the CDK 1 specific activity and the CDK 2 specific activity, and the p21 expression level, all of which offer the basis for each determination, are indicated together with the results of determining the recurrence risk or sensitivity levels depending on the selection mode selected (step S48).

For the values for the fourth to seventh thresholds, the threshold values described in PCT/JP No. 009847/2005 and JA No. 158373/2005 may be used. For the fourth threshold, it is preferable to use the value identical to that of the first threshold.

Figure 28:
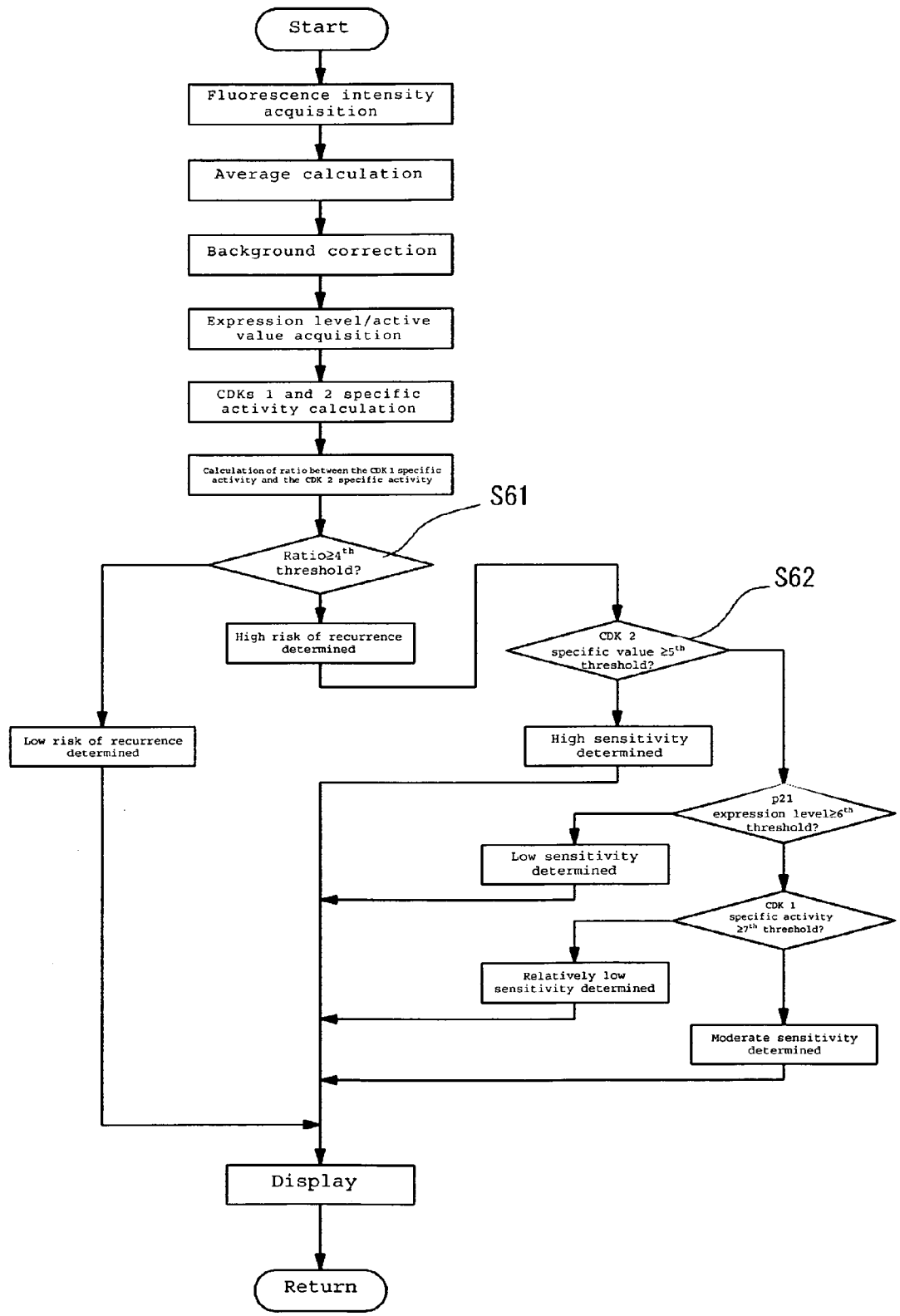
FIG. 28 is a view showing an overall flow of another example of the analysis process by the determination apparatus.

FIG. 28 shows the flow of the other embodiment of the analytical process shown in FIG. 27. In this embodiment, a step of accepting the selected mode is not involved in the step S1 in FIG. 17. In the step S61, the risk of recurrence is determined. Only the specimens, for which the risk of recurrence is determined to be high, the sensitivity to anticancer drugs is determined (step S62). Other steps are identical to those shown in FIG. 27.

According to the embodiments, the determination apparatus A may determine the risk of recurrence and the sensitivity of the tissues to anticancer drugs. However, not limited to this type of apparatus, the present invention may be applied to the determination apparatus capable of executing only one of these functions.

What is claimed is:

1. A tissue characteristic determination apparatus for determining a characteristic of tissue collected from a living organism comprising:
   a first sample processor configured for processing a sample prepared from the tissue to prepare an activity measuring sample;
   a second sample processor configured for processing the sample prepared from the tissue to prepare an expression level measuring sample;
   a first data obtainer for obtaining first data reflecting an activity of a first cyclin-dependent kinase (CDK) from the activity measuring sample prepared by the first sample processor;
   a second data obtainer for obtaining second data reflecting an expression level of a first CDK from the expression level measuring sample prepared by the second sample processor; and
   a tissue characteristic information obtainer for obtaining information on the characteristic of the tissue based on the first and second data.

2. The tissue characteristic determination apparatus according to claim 1, wherein the first processor processes the sample to prepare a second activity measuring sample and the second processor processes the sample to prepare a second expression level measuring sample, and wherein the tissue characteristic determination apparatus further comprises:
   a third data obtainer for obtaining third data reflecting an activity of a second CDK from the second activity measuring sample prepared by the first sample processor; and
   a fourth data obtainer for obtaining fourth data reflecting an expression level of a second CDK from the second expression level measuring sample prepared by the second sample processor;
   wherein the tissue characteristic information obtainer obtains the information on the characteristic of tissue based on the first, second, third, and fourth data.

3. The tissue characteristic determination apparatus according to claim 2, wherein the tissue characteristic information obtainer obtains a first value based on the first and second data, a second value based on the third and fourth data, and the information on the characteristic of the tissue by comparing the ratio between the first and second values with a first threshold.

4. The tissue characteristic determination apparatus according to claim 2, wherein the tissue characteristic information obtainer comprises:
   a first activity value obtainer for obtaining a first CDK activity value from the first data;
   a first expression level obtainer for obtaining a first CDK expression level from the second data;
   a second activity value obtainer for obtaining a second CDK activity value from the third data; and
   a second expression level obtainer for obtaining a second CDK expression level from the fourth data;
   wherein the tissue characteristic information obtainer obtains a first value based on the first CDK activity value and the first CDK expression level and obtains a second value based on the second CDK activity value and the second CDK expression level.

5. The tissue characteristic determination apparatus according to claim 4, further comprising:
   a conversion data store for storing a first conversion data used in converting the first data into the first CDK activity value; a second conversion data used in converting the second data into the first CDK expression level; a third conversion data used in converting the third data into the second CDK activity value; a fourth conversion data used in converting the fourth data into the second CDK expression level,
   wherein
   the first activity value obtainer obtains the first CDK value from the first data based on the first conversion data,
   the first expression level obtainer obtains the first CDK level from the second data based on the second conversion data,
   the second activity value obtainer obtains the second CDK activity value from the third data based on the third conversion data, and
   the second expression level obtainer obtains the second CDK expression level from the fourth data based on the fourth conversion data.

6. The tissue characteristic determination apparatus according to claim 4,
   wherein the tissue characteristic information obtainer obtains a first ratio between the first CDK activity value and the first CDK expression level as the first value and the second ratio between the second CDK activity value and the second CDK expression level as the second value.

7. The tissue characteristic determination apparatus according to claim 2,
   wherein the first CDK is CDK 1 and the second CDK is CDK 2.

8. The tissue characteristic determination apparatus according to claim 1,
   wherein the information on characteristic of the tissue is proliferation potency or malignancy revel of cells contained in the tissue.

9. The tissue characteristic determination apparatus according to claim 8,
   wherein the information on characteristic of the tissue is used in determining appropriate therapy.

10. The tissue characteristic determination apparatus according to claim 1,
    wherein the tissue characteristic information obtainer obtains a first value based on the first and second data and obtains the information on the characteristic of the tissue by comparing the first value with a second threshold.

11. The tissue characteristic determination apparatus according to claim 1,
    wherein the tissue characteristic information obtainer comprises a first activity value obtainer for obtaining a first CDK activity value from the first data, a first expression level obtainer for obtaining a first CDK expression level from the second data, and obtains the first value based on the first CDK activity value and the first CDK expression level.

12. The tissue characteristic determination apparatus according to claim 11, further comprising:
a conversion data store for storing a first conversion data used in converting the first data into the first CDK activity value and the second conversion data used in converting the second data into the second CDK activity value,
wherein the first activity value obtainer obtains the first CDK activity value from the first data based on the first conversion data,
the first expression level obtainer obtains the first CDK expression level from the second data based on the second conversion data.

13. The tissue characteristic determination apparatus according to claim 11, wherein the tissue characteristic information obtainer obtains a ratio between the first CDK activity value and the first CDK expression level.

14. The tissue characteristic determination apparatus according to claim 1, wherein the second processor processes the sample to prepare a third expression level measuring sample, and wherein the tissue characteristic determination apparatus further comprises:
a fifth data obtainer for obtaining fifth data reflecting CDK inhibitor expression level from the third expression level measuring sample;
wherein the tissue characteristic information obtainer obtains information on the characteristic of the tissue based on the first, second, and fifth data.

15. The tissue characteristic determination apparatus according to claim 14, wherein the tissue characteristic information obtainer further comprises a third expression level obtainer for obtaining the CDK inhibitor expression level from the fifth data and obtains a first value based on the first and second data and the information on the characteristic of the tissue based on the first value and the CDK inhibitor expression level.

16. The tissue characteristic determination apparatus according to claim 15, wherein The tissue characteristic information obtainer obtains the information on the characteristic of the tissue by comparing the first value with a second threshold and the CDK inhibitor expression level with a third threshold.

17. The tissue characteristic determination apparatus according to claim 1, wherein the characteristic of the tissue is sensitivity to irritant.

18. The tissue characteristic determination apparatus according to claim 17, wherein the characteristic of the tissue is used in determining the use of anticancer drug.

19. The tissue characteristic determination apparatus according to claim 1, further comprising:
a first reactor for reacting a substrate solution containing a substrate of the first CDK with the first CDK,
wherein the first data obtainer obtains the first data by detecting a first label added to a substance produced by the reaction.

20. The tissue characteristic determination apparatus according to claim 1, further comprising:
a second reactor for reacting antibody solution containing a first CDK antibody with the first CDK,
wherein the second data obtainer obtains the second data by detecting a second label added to the antibody.

21. A tissue characteristic determination apparatus for determining the characteristic of tissue, which is capable of operating in any of a plurality of operation modes, comprising:
a first sample processor configured for processing a sample prepared from the tissue to prepare an activity measuring sample;
a second sample processor configured for processing the sample prepared from the tissue to prepare an expression level measuring sample;
a data obtainer for obtaining data reflecting CDK activity value from the prepared activity measuring sample or CDK expression level from the prepared expression level measuring sample;
a first tissue characteristic information obtainer for obtaining information on proliferation potency or malignancy level of cells contained in the tissue based on the data obtained by the data obtainer;
a second tissue characteristic information obtainer for obtaining information on sensitivity of the tissue to irritant based on the data obtained by the data obtainer; and
a mode selector for selecting operation mode from a first operation mode and a second operation mode, the first operation mode using the first tissue characteristic information obtainer and the second operation mode using the second tissue characteristic information obtainer.

22. The tissue characteristic determination apparatus according to claim 21, wherein the data contains a first data reflecting a CDK activity value and a second data reflecting a CDK expression level.

23. The tissue characteristic determination apparatus according to claim 22, wherein the first data contains a third data reflecting a first CDK activity value and a fourth data reflecting a first CDK expression level and the second data contains a fifth data reflecting a second CDK activity value and a sixth data reflecting a second CDK expression level and the first tissue characteristic information obtainer obtains the information on the proliferation potency and malignancy level of cells based on the third, fourth, fifth, and sixth data.

24. A tissue characteristic determination apparatus for determining a characteristic of tissue, comprising:
a first data obtainer for obtaining first data reflecting a first CDK activity value contained in a sample prepared from the tissue;
a second data obtainer for obtaining second data reflecting a first CDK expression level contained in the sample;
a first sample processor for applying a predetermined process to the tissue to obtain the first data by the first data obtainer;
a second sample processor for applying a predetermined process to the tissue to obtain the second data by the second data obtainer;
a tissue characteristics information obtainer for obtaining information on the characteristic of the tissue based on the first and second data; and
a controller for controlling operations of the first and second sample processor so that the processing in both the first and second sample processor is executed in parallel.

* * * * *